US006303290B1

(12) United States Patent
Liu et al.

(10) Patent No.: US 6,303,290 B1
(45) Date of Patent: *Oct. 16, 2001

(54) ENCAPSULATION OF BIOMATERIALS IN POROUS GLASS-LIKE MATRICES PREPARED VIA AN AQUEOUS COLLOIDAL SOL-GEL PROCESS

(75) Inventors: Dean-Mo Liu, Richmond (CA); I-Wei Chen, Swarthmore, PA (US)

(73) Assignee: The Trustees of the University of Pennsylvania

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/661,122

(22) Filed: Sep. 13, 2000

(51) Int. Cl.[7] ............................. C12Q 1/00; C12Q 1/68; G01N 33/552
(52) U.S. Cl. .................................. 435/4; 435/6; 436/527
(58) Field of Search ............................. 435/6, 4; 436/527

(56) References Cited

U.S. PATENT DOCUMENTS 5,252,318  10/1993  Joshi et al. .
5,441,732   8/1995  Hoeg et al. .

FOREIGN PATENT DOCUMENTS

WO 97/21441  7/1997  (WO) .

OTHER PUBLICATIONS

Dave, B.C. et al., "Sol–Gel Encapsulation Methods for Biosensors", Analytical Chemistry, vol. 66, pp. 1120A–1127A (1994).*

Avery RG, JDF Ramsay "The Sorption of Nitrogen in Porous Compacts of Silica and Zirconia Powders" *J. Colloid and Interface Sci.* 42(3):597–606 (1973).
Aso Y, S Yoshioka, Y Nakai, S Kojima "Thermally controlled protein release from gelatin–dextran hydrogels" *Radiation Physics and Chem.* 55:179–183 (1999).

(List continued on next page.)

Primary Examiner—Kenneth R. Horlick
Assistant Examiner—Teresa Strzelecka
(74) Attorney, Agent, or Firm—Evelyn H. McConathy; Dilworth Paxson LLP

(57) ABSTRACT

The present invention provides a process for the encapsulation of biologically important proteins into transparent, porous silica matrices by an alcohol-free, aqueous, colloidal sol-gel process, and to the biological materials encapsulated thereby. The process is exemplified by studies involving encapsulated cytochrome c, catalase, myoglobin, and hemoglobin, although non-proteinaceous biomaterials, such as active DNA or RNA fragments, cells or even tissues, may also be encapsulated in accordance with the present methods. Conformation, and hence activity of the biomaterial, is successfully retained after encapsulation as demonstrated by optical characterization of the molecules, even after long-term storage. The retained conformation of the biomaterial is strongly correlated to both the rate of gelation and the subsequent drying speed of the encapsulatng matrix. Moreover, in accordance with this process, gelation is accelerated by the use of a higher colloidal solid concentration and a lower synthesis pH than conventional methods, thereby enhancing structural stability and retained conformation of the biomaterials. Thus, the invention also provides a remarkable improvement in retaining the biological activity of the encapsulated biomaterial, as compared with those involved in conventional alkoxide-based processes. It further provides new methods for the quantitative and qualitative detection of test substances that are reactive to, or catalyzed by, the active, encapsulated biological materials.

21 Claims, 16 Drawing Sheets

OTHER PUBLICATIONS

Barker SLR, R Kopelman, TE Meyer, MA Cusanarich "Fiber–Optic Nitric Oxide–Selective Biosensors and Nanosensors" *Anal. Chem.* 70(5):971–976 (1998).

Bescher E, JD Mackenzie "Hybrid organic–inorganic sensors" *Mater. Sci. & Eng.* C 6: 145–154 (1998).

Böttcher H, P Slowik, W. Süb "Sol–Gel Carrier Systems for Controlled Drug Delivery" *J. Sol–Gel Sci, and Tech.* 13:227–281 (1998).

Coche–Guérente L, S Cosnier, P Labbé "Sol–Gel Derived Composite Materials for the Construction of Oxidase/Peroxidase Mediatorless Biosensors" *Chem. Mater.* 9:1348–1352 (1997).

Dave BC, H Soyez, JM Miller, B Dunn, JS Valentine, JI Zink "Synthesis of Protein–Doped Sol–Gel $SiO_2$ Thin Films: Evidence for Rotational Mobility of Encapsulated Cytochrome c" *Chem. Mater.* 7:1431–34 (1995).

Dave BC, B Dunn, JS Valentine, JI Zink "Sol–Gel Encapsulation Methods for Biosensors" *Ana. Chem.* 66(22):1121A–1127A (1994).

Demochenku AP *Ultraviolet Spectroscopy of Proteins* Chap. 3&4, Springer–Verlag Berlin (1981).

Dunn B, JM Miller, BC Dave, JS Valentine, JI Zink "Strategies For Encapsulating Biomolecules in Sol–Gel Matrices" *Acta Mater.* 46(3):737–741 (1998).

Dumortier G, JL Grossiord, M Zuber, G Couarraze, JC Chaumeil "Rheological Study of a Thermoreversible Morphine Gel" *Drug Dev. and Indus. Phar.* 17(9):1255–1265 (1991).

Edsman K, J Carlfors, R Petersson "Rheological evaluation of poloxamer as an in situ gel for ophthalmic use" *Eur. J. Pharm. Sci.* 6:105–112 (1998).

Ellerby LM, CR Nishida, F Nishida, SA Yamanakas, B Dunn, JS Valentine, JI Zink "Encapsulation of Proteins in Transparent Porous Silicate Glasses Prepared by the Sol–Gel Method" *Science* 255:1113–1115 (1992).

Eom GT, SY Oh, TS Park "In Situ Thermal Gelation of Water–Soluble Poly (N–isopropylacrylamide–co–vinylphosphonic acid)" *J. Applied Polymer Sci.* vol. 70:1947–1953 (1998).

Esposito E, V Carotta, A Scabbia, L Trombelli, P D'Antona, E Menegatti, C Nastruzzi "Comparative analysis of tetracycline–containing dental gels: poloxamer–and monoglyceride–based formulations" *Int. J. of Pharm.* 142:9–23 (1996).

Gekko K, H Hasegawa "Compressibility–Structure Relationship of Globular Proteins" *Biochemistry* 25:6563–6571 (1986).

Glezer V, O Lev "Sol–Gel Vanadium Pentaoxide Glucose Biosensor" *J. Am. Chem. Soc.* 115:2533–2534 (1993).

Haglund BO, R Joshi, KJ Himmelstein "An in situ gelling system for parenteral delivery" *J. Controlled Release* 41:229–235 (1996).

Huang Y, MD Donovan "Modifications of the Sol–Gel Transition Temperature and Gelling Time of Pluronic F127 Using Ionic and Non–Ionic Additives" College of Pharmacy, Univ. of Iowa, Iowa City, IA 52242 (PT 6224).

Jeong B, YHB Bae, DS Lee, SW Kim "Biodegradable Thermosensitive Hydrogel" Dept. of Pharm. and Pharm. Chem./Cntr for Controlled Chem. Del., Univ. of Utah, Salt Lake City, UT 84112 (PDD 7402).

Klein LC "Sol–Gel Processing of Silicates" *Ann. Rev. of Mater. Sci.* 15:227–248 (1985).

Kondo A, J Mihara "Comparison of Adsorption and Conformation of Hemoglobin and Myoglobin on Various Inorganic Ultrafine Particles" *J. Colloid and Interf. Sci.* 177:214–221 (1996).

Kurokawa Y, T Sano, H Ohta, Y Nakagawa "Immobilization of Enzyme onto Cellulose–Titanium Oxide Composite Fiber" *Biotech. and Bioengineering* 42:394–397 (1993).

Kurisawa M, N Yui "Dual–stimuli–responsive drug release from interpenetrating polymer network–structured hydrogels of gelatin and dextran" *J. Controlled Release* 54:191–200 (1998).

Lan EH, B Dunn, JS Valentine, JI Zink "Encapsulation of the Ferritin Protein in Sol–Gel Derived Silica Glasses" *J. Sol–Gel Sci. Tech.* 7:109–116 (1996).

Lan EH, BC Dave, JM Fukuta, B Dunn, JI Zink, JS Valentine "Synthesis of sol–gel encapsulated heme proteins with chemical sensing properties" *J. Mater. Chem.* 9:45–53 (1999).

Livage J, C Roux, JM Costa, I Desportes, JF Quinson "Immunoassays in Sol–Gel Matrices" *J. Sol–Gel Sci. Tech.* 7:45–51 (1996).

Miller JM, B Dunn, JS Valentine, JI Zink "Synthesis conditions for encapsulating cytochrome c and catalase is $SiO_2$ sol–gel materials" *J. Non–Crystalline Solids* 202:279–289 (19986).

Myer YP, A Pande *Circular Dichroism Studies of Hemoproteins and Heme Models The Porphyrins* (D. Dolphin ed.) vol. 3:271–317 (1978).

Narang U, PN Paras, FV Bright "Glucose Biosensor Based on a Sol–Gel–Derived Platform" *Anal. Chem.* 66(19):3139–3144 (1994).

Nicola NA, SJ Leach "Interpretation and Applications of Thermal Difference Spectra of Proteins" *Int. J. Peptide Protein Res.* 8:393–415 (1976).

Peterson KP, CM Peterson, EJ Pope "Silica Sol–Gel Encapsulation of Pancreatic Islets" *Proc. Soc. Exp. Biol. Med.* 218:365–369 (1998).

Safer MW, DD Awschalom, J Warnock, G Ruben "The chemistry of and physics with porous sol–gel glasses" *J. Appl. Phys.* 61(12):5438–5446 (1987).

Tatsu Y, K Yamashita, M Yamaguchi, S Yamamura, H Yamamoto, S Yoshikawa "Entrapment of Glucose Oxidase in Silica Gel by the Sol–Gel Method and its Application to Glucose Sensor" *Chem. Letters* 1615–1618 (1992).

* cited by examiner

ENCAPSULATION OF BIOMATERIALS IN POROUS GLASS-LIKE MATRICES PREPARED VIA AN AQUEOUS COLLOIDAL SOL-GEL PROCESS

GOVERNMENT INTERESTS

This invention was supported in part by the U.S. Department of Energy (BES) under Grant No. DE-FG02-97ER45637 A001. The Government may have certain rights in this invention.

FIELD OF THE INVENTION

The invention relates to the process of preparing a porous, inorganic, glass-like matrix by an alcohol-free, aqueous colloidal sol-gel process, and the encapsulation therein of an active biological material, and to the nanocomposite prepared by such processes, and to the qualitative and quantitative detection of a test substance in a gas or aqueous solution when it is brought into contact with the encapsulated active biomaterial in the nanocomposite.

BACKGROUND OF THE INVENTION

Biological molecules such as proteins, biopolymers, and enzymes including cytochrome c, catalase, ferriten, antibiotics, myoglobin, hemoglobin, and the like have been encapsulated into porous, inorganic host matrices, including transparent glasses and/or oxides (Bescher and Mackenzie, *Mat. Sci. Eng.*, C6:145–154 (1998); Messing, *Immobilized Enzymes for Industrial Reactors*, Academic Press, New York (1975)). The metal alkoxide based process is the conventional choice for preparing an inorganic/organic hybrid at low temperatures (Klein, *Annual Review of Materials Science*, p. 227, Huggins et al., ed., Vol.15, (Palo Alto Calif.), 1985; Brinker and Scherer, *Sol-Gel Science: The Physics and Chemistry of Sol-Gel Processing*, Academic, Boston, 1990). The fragile characteristics of protein biomolecules limit the synthesis of inorganic/biomolecule composites to a sol-gel process for encapsulating the biological material into transparent silica matrices, which are capable of responding at a temperature significantly below the conventional sintering or melting temperature of the inorganics (Ellerby et al., *Science* 255:1113–15 (1992)); U.S. Pat. No. 5,200,334 ("Dunn et al. '334 patent")).

The basic concept of the sol-gel process involves hydrolysis and polymerization of inorganic monomers, typically using metal alkoxides, such as tetramethyl orthosilicate (TMOS) or tetraethyl orthosilicate (TEOS). The biomolecules are added to and dispersed within the solution, to which a buffer solution has been introduced to adjust the solution pH to a level suitable for biomolecule survival. Hydrolysis of the alkoxide, e.g., TMOS, in the presence of water, an organic solvent and an acid/base catalyst results in the formation of —Si—OH bond. As the metal oxides undergo hydrolysis and polymerization reactions, the —Si—OH, silanol bonds further polymerize into —Si—O—Si— bonds, and an inorganic three-dimensional network finally develops within a firm gel. As the gel dries, it shrinks and hardens further into an inorganic matrix (sometimes referred to as an aerogel) with a pore size typically in the range of 2–5 nm. The residue solvents are expelled from the growing network and the dispersed biomolecules are finally trapped into network cages (Dave et al., *Ana. Chem.* 66[22]:1120A–1127A (1994)). After a relatively long period of time, e.g., a few weeks, the solvent evaporates to result in a biomolecule-doped, transparent, dried matrix (Ellerby et al., 1992).

The biological molecules entrapped within the matrices reportedly retain high-levels of biological activity (Ellerby et a., 1992; Miller et al., *J. Non-Crystalline Solids* 202:279–289 (1996); Narang et aL, *Ana. Chem* 66[19]:3139 (1994); Livage et al., J. Sol-Gel Sci. Tech. 7:45–51 (1996); Coche-Guerente et at., *Chem. Alater.* 9: 1348–52 (1997); Kurokawa et al., *Biotech. Bioengineer.* 42:394–397 (1993); Glezer and Lev, *J. Am. Chem. Soc.* 115:2533–34 (1993); Tatsu et at., *Chem. Letters* 1615–1618 (1992); Lan et al., *J. Sol-Gel Sci. Tech.* 7:109–116 (1996)). Presumably, this is because the native-state conformation of the encapsulated molecule is sufficiently retained to permit a degree of measurable activity. Meanwhile, the matrix pores allow the diffusion of reactant molecules and their reaction with the entrapped biomolecules. Through these reactions, the biomolecule-containing inorganic monolith materials possess an ability to detect other molecules, and can thus be used as sensors for optical, electrical, mechanical or chemical signals (Bescher and Mackenzie,1998; Bakul et al.,*Ana. Chem.* 66[22]:1121A (1994)).

Both the gel and aerogel are typically, to a certain extent, transparent to visible light and permeable to gases, wetting agents, ions and small molecules. Thus, the structure and properties of encapsulated biomolecules can be examined via spectroscopic means. Unfortunately, however, although reports have indicated the successful retention of up to 80% of the protein activity, the presence of alcohol in these alkoxide-based sol-gel processes has been known to denature proteins, thereby causing chain unfolding, aggregation, and destruction of secondary and tertiary protein structures to a significant extent (Miller et al.,*J. Non-Crystalline Solids* 202:279–289 (1996)).

Alcohol is known to be lethal to many higher level biomolecules that have more delicate structures and more complicated functions, and it may impair the activity of other biomolecules to some extent even when they survive. Although the TMOS method by Ellerby et al., 1992 and the Dunn et al. '334 patent claim to use a "non-alcoholic medium," and teach that the addition of alcohol is not necessary to form the sol, any use of a metal alkoxide will release alcohol during hydrolysis. For example, in the case of TMOS, methanol is released according to the following reaction: $Si(OMe)_4 + H_2O \rightarrow Si(OMe)_{4-x}(OH)_x + x\ CH_3OH$.

In the preceding reaction, Me represents the $CH_3$ group. The methanol ($CH_3OH$) content, x, increases with the extent of hydrolysis. When hydrolysis is complete, a maximum of 4 moles of methanol is released for every mole of TMOS hydrolyzed. Since hydrolysis is the basis of the TMOS sol-gel method taught by Ellerby et al., 1992 and by the Dunn et al.'334 patent, alcohol always exists in the composite once the hydrolysis reaction begins. This is easily verified by the smell of alcohol that always accompanies any product of an alkoxide reaction, even though no alcohol has been expressly added.

The damaging effect of alcohol in the process is clear. For example, Miller et al., 1996, have reported a 70% reduction of the enzymatic activity when bovine liver catalase was encapsulated into a TMOS-based silica matrix, with merely 5 vol% methanol present. Moreover, a number of spectroscopic studies on protein denaturation have found an altered intensity and longwave shift of the absorption spectra when polar perturbing solvents, such as alcohols, interact with the aromatic amino acid residues of the proteins (Herkovits and Sorensen, *Biochemistry,* 7:2523–2533 and 2533–2542 (1968); Izumi and Inoue, *J. Biochem.* (Tokyo), 79, 1309–1321 (1976); Timasheff and Inoue, *Biochemistry,* 7:2501–2513 (1968); and Strickland et al., *Biochemistry* 11:3657–3662 (1972)).

Accordingly, until the present invention, there has been a long-felt need in the art for the development of an alcohol-free, sol-gel process for the encapsulation of active, biological materials in a visually transparent porous, inorganic matrix, thereby preventing the denaturation of biomolecule caused by the undesirable interaction with the alcohol molecules and the extent of conformational change reduced, particularly for fragile biomolecules.

SUMMARY OF THE INVENTION

The present invention, therefore, meets a particular need in the art by providing an alcohol-free, aqueous, colloidal sol-gel process for the encapsulation of active, biological materials in a preferably visually transparent matrix. The proteins or biomolecules are immobilized, but they retain their biofunctions, reacting with incoming ions or solutions that diffuse through the porous matrix. Such reactions are often readily detectable by the change in the optical absorption resulting in a change of color. Therefore, these composites can be used as biosensors for gas and liquid species.

A similar class of hybrid composites incorporating enzymes and other biopolymers can be used for bioreactors for energy generation and other reactions. The encapsulated biomolecules may also assume other functions normally performed by proteins, including synthesis, regulation and repair of other molecules, and the identification and targeting of host and foreign molecules for destruction. They may thus also play a role in drug delivery, bioimplants, and human repair processes. They can also be sufficiently robust for use in manufacturing and industrial settings as bioreactors in energy, agricultural, e.g., photosynthesis and bioremediation, and environmental applications.

Since the encapsulation method of the present invention is based upon an aqueous, alcohol-free sol-gel, it avoids the problems associated with the conventional silica-based, metal alkoxide methods, which require the addition or release of alcohol in the course of the reaction. Thus, in accordance with the present method, contact with alcohol is completely eliminated throughout the reaction, thereby avoiding the alcohol-caused denaturalization of many biopolymers (caused by chain unfolding or molecule aggregation), typically seen in the conventional encapsulation methods. Consequently, the types of biopolymers that can be incorporated in these composites are essentially unlimited.

The present invention provides an alcohol-free method of making a porous, inorganic matrix containing a biological material encapsulated therein, comprising: (a) forming an aqueous composition comprising a ceramic oxide colloidal sol mixed with an acidified oxide salt solution, which is transformed into a polymerizing hydroxide solution, and wherein the resulting composition has a pH ranging from 6.2 to 8.2; (b) adding to said composition an amount of the biological material in a physiologically acceptable-buffered solution to form a nanocomposite, wherein the ionic strength of the resulting nanocomposite is adjusted to a physiologically acceptable level by the addition of salts; (c) gently shaking the resulting nanocomposite until it becomes viscous; (d) shaping the viscous, aqueous mixture produced in step (c) into a final form and aging into an aqueous gel; and (e) drying the aged gel slowly in air at a temperature of ~4° C., thereby permitting a portion of the water in the gel to evaporate, wherein the drying gel has a decreased volume as compared with the aged gel of step (d), and molecules of the biological material are encapsulated within pores of the drying or dried gel.

In a preferred embodiment, the present invention provides the method wherein the nanocomposite is comprised of colloidal silica sol and dissolved sodium silicate.

The invention further provides the method, wherein the size of the sol particle is selected to produce a pore size when the gel is dried, which is essentially the same as the size of a molecule of the encapsulated biological material.

The invention also provides the method, wherein the biological material is selected from the group consisting of RNA, DNA, active proteins, active fragments of DNA, RNA, or proteins, and cells or tissues. In a preferred embodiment of the present invention, the biological material is any active protein or active fragment thereof. More specifically, the protein or active fragment thereof is a member of a family or group of enzymes or active compounds, including, but not limited only to any RNase, DNase, nuclease, ribonuclease; hydrogenase, dehydrogenase, aldase, amidase, aminotransferase, amylase, anhydrase, apyrase, arginase, aspartase, aspariginase, carboxylase, carboxypeptidase, catalase, cellulase, cholinesterase, acetylcholinesterase, deaminase, dextranase, dismutase, elastase, esterase, fumarase, glucosidase, hexokinase, isomerase, invertase, kinase, lactase, lipase, lysozyme, malase, naringinase, oxidase, oxygenase, papain, pectinase, peptidase, pepsin, peroxidase, phosphodiesterase, phosphotase, protease, reductase, transferase, tyrosinase, urase, cholesterol, trypsin, chymotrypsin, enzyme, immunoglobulin, and combinations thereof.

In addition, the biological material can include any protein or biomaterial acted upon by such enzymes or active compounds. As exemplified, the method is provided, wherein the protein is selected from the group consisting of cytochrome c, catalase, myoglobin, and hemoglobin.

The invention provides embodiments, wherein the aqueous gel is shaped, preferably into a monolithic gel, thin film, or fiber.

The invention also provides embodiments, wherein the dried gel comprises pores having an average diameter ranging from 1 nm to 100 nm, or more preferably ranging from 2 nm to 50 nm. More specifically, the pores of the dried gel comprise a matrix having pores of approximately the same dimension as the molecules of biological material encapsulated therein.

The invention further provides an alcohol-free, porous, inorganic, colloidal sol-gel nanocomposite having encapsulated therein an active biological material, wherein the nanocomposite is prepared in accordance with the methods provided herein. In a preferred embodiment of the present invention, the nanocomposite is prepared comprising colloidal silica sol and dissolved sodium silicate. The preferred encapsulated biological material within the nanocomposite is an RNA, DNA, or protein, or an active fragment of DNA, RNA, or proteins, as well as cells or tissues. The more preferred encapsulated biological material is any active protein or active fragment thereof.

In addition, the invention provides for the use of a nanocomposite comprising an active biological material encapsulated therein, to quantitatively or qualitatively detect a test substance that reacts with or whose reaction is catalyzed by said encapsulated active biological material.

Also provided is a method for the quantitative or qualitative detection of a test substance that reacts with or whose reaction is catalyzed by an active biological material, wherein said biological material is encapsulated within a nanocomposite, and wherein said nanocomposite comprises a porous, inorganic matrix prepared by an alcohol-free colloidal sol-gel method. The quantitative/qualitative method comprises (a) preparing the nanocomposite comprising said active biological material encapsulated within a porous, inorganic matrix prepared by an alcohol-free colloidal sol-gel method; (b) bringing said biological-material-containing nanocomposite into contact with a gas or aqueous solution comprising the test substance; and (c) quantitatively or qualitatively detecting, observing or measuring the change in one or more optical characteristics in the biological material encapsulated within the nanocomposite.

In particular, the invention provides a method, wherein the change in one or more optical characteristics of the encapsulated biological material is qualitatively or quantitatively measured by spectroscopy, utilizing one or more techniques selected from the group consisting of UV, IR, visible light, fluorescence, luminescence, absorption, emission. excitation and reflection.

In addition, the invention provides a method of storing a biological material in a porous, inorganic matrix, wherein more than 80% of the biological activity of the material is retained for long periods of time, under adverse conditions. Also provided is a method of storing a biologically active biological material in a porous, inorganic matrix, wherein the biological material is an active protein or active protein fragment, wherein the nanocomposite comprises colloidal silica sol and dissolved sodium silicate, and wherein more than 80% of the biological activity of the protein or protein fragment is retained for long periods of time under adverse conditions.

The invention will be more fully understood from the following detailed description of preferred embodiments, drawings and examples, all of which are intended to be for illustrative purposes only, and not intended in any way to limit the invention.

BRIEF DESCRIPTION OF THE FIGURES

FIG. 12A shows the effect of methanol; and FIG. 12B shows the effect of ethanol. In each case, the gel was soaked for 24 hrs in the methanol or ethanol, respectively.

DETAILED DESCRIPTION OF THE INVENTION

Figure 1:
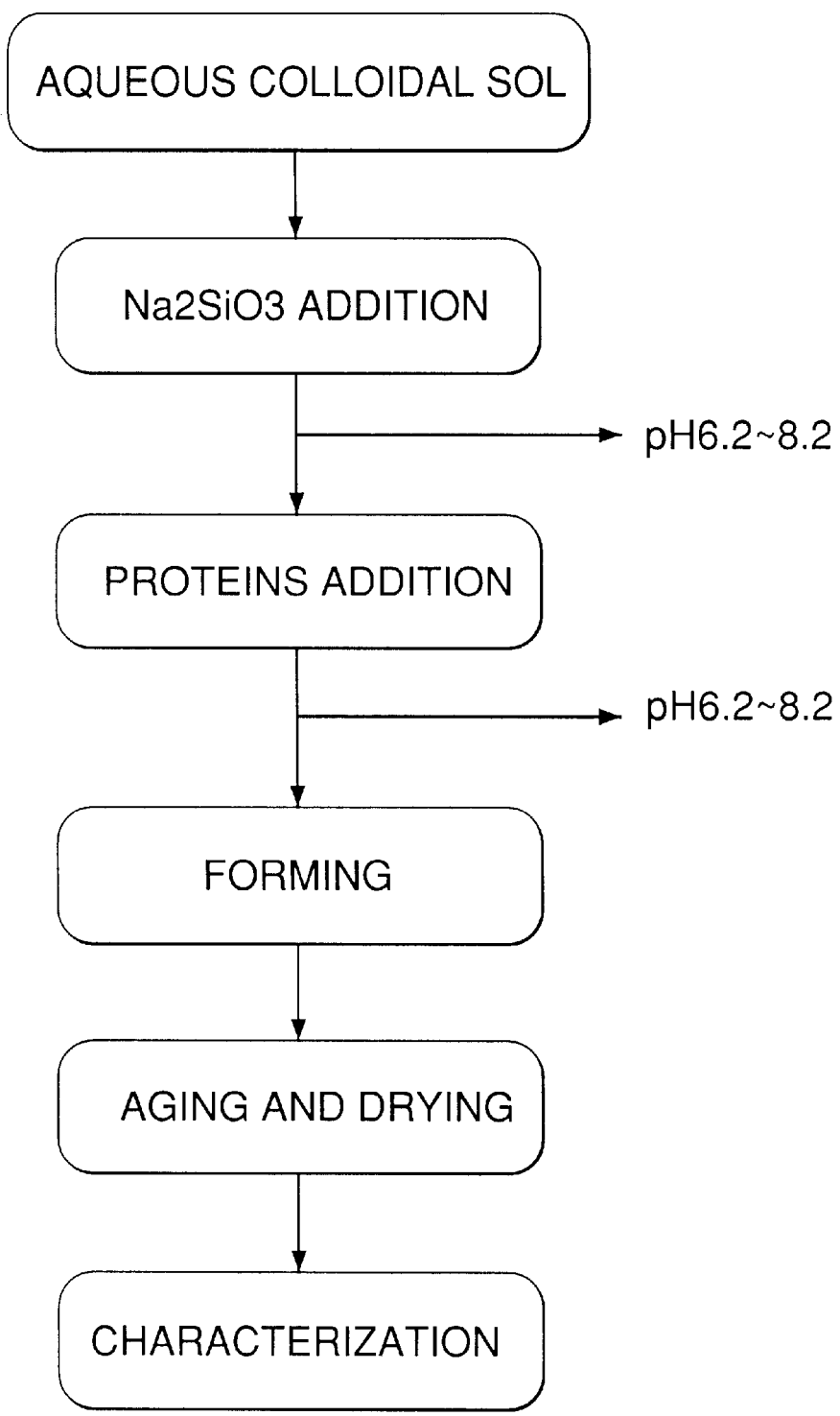
FIG. 1 depicts a flow-chart showing the aqueous colloidal sol-gel encapsulation process.

Encapsulation of active biological molecules into porous, preferably transparent, silica matrices has been successfully achieved by the alcohol-free, aqueous, colloidal sol-gel process of the present invention. The entrapped proteins demonstrate better conformational stability in comparison to those entrapped using conventional alkoxide-based sol-gel processes, and the effect is significantly enhanced when the rates of both gelation and drying are increased and when the pore size is decreased. The abrupt arrest of the protein mobility upon gelation of the surrounding matrix, which is then fixed as the matrix shrinks and dries, accounts for the observed protein stability and its dependence on processing conditions. Meanwhile, the pore space remains sufficient to allow smaller ions and molecules to penetrate and react with or be catalysed by the encapsulated active biomaterials. The advantageous effects of the present invention is further evidenced by a remarkable improvement in enzymatic activity in proteins encapsulated by the present process, as compared with encapsulation using conventional, TMOS - based processes.

The gelation process can be controlled to obtain different viscosities so that the liquid can be shaped e.g., into monoliths, thin films or fibers, which become transparent after drying. Optical absorption spectroscopy has verified that the proteins are completely active after encapsulation, as their characteristic absorption band shows neither a shift in energy, nor a decrease in absorbance at any stage of the hybrid preparation. Thus, the biomolecule-containing inorganic materials can be used to detect molecules and act as sensors.

For the purposes of this invention, the terms "protein," "enzyme," "biomolecule," "biomaterial" and "biopolymer"

are used essentially interchangeably with regard to the aqueous alcohol-free, sol-gel method and resulting composition. It is, however, recognized that, in fact, the terms represent several classes of molecules. For example, biomaterials, biomolecules and biopolymers can refer to either proteinaceous or non-proteinaceous molecules or compounds, the latter of which includes, but is not limited to, nucleotides and nucleosides. Enzymes arc a specific subset of proteins, having specialized catalytic functions.

In accordance with a preferred embodiment of the present invention, the encapsulated biomaterials are active proteins or active protein fragments. The active protein or active protein fragment may be any protein, peptide, polypeptide or proteinaceous biomaterial, so long as it has measurable activity by standard means. For example, although not intending to be limiting, the active protein or active protein fragment can be selected from among the following families of proteins: any RNase, DNase, nuclease, ribonuclease; hydrogenase, dehydrogenase; aldase, amidase, aminotransferase, amylase, anhydrase, apyrase, arginase, aspartase, aspariginase, carboxylase, carboxypeptidase, catalase, cellulase, cholinesterase, acetylcholinesterase, deaminase, dextranase, dismutase, elastase, esterase, fumarase, glucosidase, hexokinase, isomerase, invertase, kinase, lactase, lipase, lysozyme, malase, naringinase, oxidase, oxygenase, papain, pectinase, peptidase, pepsin, peroxidase, phosphodiesterase, phosphotase, protease, reductase, transferase, tyrosinase, urase, cholesterol, trypsin, chymotrypsin, enzyme, immunoglobulin, or antibodies or combinations thereof. The active proteins or active protein fragment may specifically include, e.g., hemoglobin, myoglobin, cytochrome c, catalase, collagen, tubulin, actin, ATPase, alcohol dehydrogenase, alcohol oxidase, alkaline phosphatase, acetylcholinesterase, albumin, aldehyde dehydrogensase, aldehyde oxidase, carbonic anhydrase, glucose oxidase, glucose isomerase, glucose dehydrogenase, beta-glucosidase, glutamate dehydrogenase, lactate dehydrogenase, malate dehydrogenase, urate oxidase, Penicillin amidase, aspartate aminotransferase, xanthine oxidase, glucoamylase, acetate kinase, pyruvate kinase, adenosin deaminase, phenol oxidase, thermotrypsin, thrombin, ferritin, polyclonal antifluorescein, immunoglobulin G (IgG), immunoglobulin M (IgM), or superperoxide dismutase.

However, every embodiment of the invention is not, and need not be, limited to protein molecules. Although full-length DNA and RNA molecules are huge in size, as compared with the exemplified, encapsulated biomaterials, active fragments of DNA or RNA are candidates for encapsulation, as are cells or even tissues. "Cells" are intended to include any known cell type, including, microorganisms, e.g., yeast, bacterial or microbes, or cells from larger organisms, e.g., animal or human cells.

Moreover, for specific applications, more than one type of selected protein can be combined within the same host matrix, or can be combined with active nucleic acid fragments (DNA or RNA) or the like. Such applications will follow known principles of size, concentration, conformation, reactivity, and the like, making their encapsulation and utilization apparent to individuals of ordinary skill in the art without burdensome experimentation in light of the disclosure and examples provided herein.

A "reactant" or "test" material or substance of the present invention refers to any biological, organic or inorganic substance in aqueous solution that reacts with, or whose reaction is catalyzed by, the active biological material encapsulated within an alcohol-free, porous, sol-gel glass-like matrix. The reaction is detectable qualitatively and measurable quantitatively when a biological material-containing glass-like nanocomposite is brought into contact with an aqueous solution or gas, comprising the reactant or test substance, and a change in one or more optical characteristics in the encapsulated material is observed or measured.

The terms "entrapped" and "encapsulated" are used interchangeably as they relate to the biological material of the present invention. The encapsulated materials are also collectively referred to as a "substrate" within the encapsulating matrix. When combined, the inorganic matrix and encapsulated biological material are referred to as a "composite," or if of selected nanometer size, as a "nanocomposite."

The alcohol-free, aqueous colloidal sol-gel process of the present invention offers a remarkable alternative to the conventional metal alkoxide sol-gel process for encapsulating biomolecules into transparent, porous matrices. This is primarily because a better retention of protein structure and biological activity is possible due to the absence of alcohol molecules. Moreover, the host matrices, through appropriate process controls, can be made optically transparent which permits spectroscopic characterization. Furthermore, the resulting host matrices protect proteins from denaturation in harsh environments. Finally, the resulting pore size can be related to the size and concentration of the starting colloidal particles, which allows optimization of the pore structure for design purposes.

By "colloidal particles" is meant small particles that are substantially in suspension in a liquid.

By "gel" is meant a colloidal solution, more specifically of a liquid in a solid. It begins in liquid form, and becomes free-standing as a result of a rapid increase of viscosity and polymerization. As it becomes viscous, it can be formed, cast, molded, shaped, spun or drawn into desired shapes. Preferred shapes for the present invention include, but are not limited to, films, fibers, monoliths, pellets, granules, tablets, rods or bulk. Particularly preferred shapes include thin-films and fibers, because gelation is enhanced, i.e., the thin layer encourages the rapid formation of the gel state (the "aged, aqueous gel" or "wet gel") from the liquid state (the "viscous aqueous mixture"). However, if the material is too fluid, it cannot retain the selected shape; but if it is too viscous, it may be difficult to form into thin films or fibers. After the "aged" gel assumes its free-standing properties, it is dried over a period of time under select conditions to lock the conformation of the gel, its pores, matrices and interconnecting channels into fixed positions and permit long term storage (the "dried gel").

By "sol" is meant a liquid that contains very fine colloidal particles.

Hydrolysis and polycondensation can in principle proceed without alcohol. Only water needs to be added and generated in the limiting circumstances. This, for example, is the case for orthosilicic acid. On the other hand, gelation can also occur in a solution of colloidal particles, either by particle percolation (at higher concentrations) or by particle bridging (at lower concentrations), without polymerization, see, e.g., Iler, *The Chemistry of Silica*, John Wiley & Sons, New York (1979). Any polycondensation reaction occurring in the background then aids gelation by forming a network around the particles, or assists in the formation of bridges between the particles. As shown, in accordance with the present invention, this process can be carried out in an aqueous solution, and thus is fully compatible with essentially all biopolymers.

In one embodiment of the present invention, the preferred methods (or "processes") are demonstrated using silica as the colloidal-particle additive and a variety of representative proteins, including enzymes, as the biopolymer "filler." Inorganic/organic nanocomposites of both monolithic gel and transparent thin film forms (obtained by spin coating) have been prepared in accordance with the present methods, and as will be shown, no structural or functional damage to the proteins has been found.

By "monolith" is meant a solid-like body in visibly one piece, from several mm in size and beyond. By "thin film" is meant a supported or unsupported layer of a thickness from 30 nm to 0.1 mm with a substantially larger cross section, typically from several mm in size and beyond.

The term "glass," although used routinely to describe porous ceramic oxide matrices, it is not well suited to define the porous matrices of the present invention. "Glass" usually refers to an inorganic substance that is non-crystalline, which is not an accurate description of all of the porous matrices that can be used in the present invention. Although the silica gel used in a preferred embodiment of the present invention, when dried, looks like a glass, even though it is porous, it is also amorphous, or non-crystalline.

Nevertheless, the process of the present invention is also applicable to and has been tested using non-silica colloidal particles, such as $TiO_2$, which are actually crystalline. Therefore, although the final matrix product may "look" like glass, it is not a true glass, and the term "glass-like" is more descriptive. Accordingly, as used in the present invention, by "transparent glass-like" inorganic substance is meant one that transmits visible light and is optically free of inclusions. A "matrix" refers to the inorganic host that forms the body of the composite containing the biomolecules. A "nanocomposite" refers to a composite of the matrix and biological material encapsulated therein, comprising species and microstructures, predominantly of a size less than 100 nm. A "xerogel" refers to a dried gel, which contains no liquid and is highly porous.

The optical clarity of the porous matrices produced by the present method is highly relevant when the encapsulated material is an enzyme, and the partially or fully dried sol-gel glass-like nanocomposite containing the encapsulated enzyme is used as a sensor. Changes in the enzyme or reactant when exposed to the sample being tested can be monitored directly using fiber optics, and the optical information can be transferred to a remote sensing instrument, such as a spectroscope, for analysis. Because of the light transmission capabilities of the porous matrices, UV, IR and visible light optical spectroscopy, as well as fluorescence, luminescence, absorption, emission, excitation and reflection techniques, are all suitable for quantifying or qualifying the chemical changes produced in the encapsulated materials of the present invention.

The present invention is not, and need not, be limited to visible or colorimetric measurements. In principle, reflection spectroscopy does not require transparency once the reaction can be detected directly in a solution. Other spectroscopic tests are known in the art, which do not rely upon the measurement of visible light. For example, the concentration change can be used to measure the activity of certain "substrate" materials (e.g., the change in oxygen concentration in a solution when encapsulated catalase enzyme was used).

The encapsulation of proteins into porous silica matrices using the alcohol-free, aqueous colloidal sol-gel process of the present invention offers a much greater retention of the active protein's native conformation than has been previously possible, thus preserving a much higher level of activity in the entrapped biomolecule. In the preferred embodiment of the present invention, more than 80%, preferably more than 85%, even more preferably more than 90%, most preferably more than 95%, and ideally as much as 100% of activity of the encapsulated biomaterial is retained, for example as shown in the case of catalase enzyme. Compared to the conventional alkoxide-based sol gel method, in which barely 80% of the activity of the encapsulated biomaterial is retained, the retained conformation of all proteins after encapsulation by the present method is clearly superior in accordance with the present invention. This advantage is attributed to the complete absence of alcohol in the aqueous colloidal process.

The advantages of the present process have been demonstrated in the encapsulation of several representative, biologically important proteins of diverse function. Hemoglobin has been selected as a model protein in the examples which follow, using UV-visible absorbance to measure changes in conformation. The findings are further supported by the enzymatic study of other enzymatic proteins, including cytochrome c, bovine liver catalase and myoglobin, encapsulated into the transparent porous silica matrices of the present invention by the alcohol-free, aqueous colloidal sol-gel process. Enzymatic activity was monitored and shown to be remarkably higher in proteins encapsulated using the alcohol-free, aqueous colloidal sol-gel process, as compared to using the conventional alkoxide-based process.

Optical characterization indicates a successful retention of protein conformation after encapsulation. Moreover, the conformation retention is strongly correlated to both the rate of gelation and the subsequent drying speed. Using model proteins, it was determined, as shown in the examples that follow, that a higher colloidal solid concentration and a lower synthesis pH, both caused faster gelation, and resulted in a better retention of conformation of the encapsulated biomolecule. Proteins encapsulated in a thin film, which dries faster, also showed a better retention than when bulk materials were used. For sensing applications, an increase in the overall response (detection) time due to reduced diffusion rates (stronger pore resistance) for target molecules is advantageous. This is the major reason for thin film development (Dave et at., *Chem. Mater.* 7:1431–34 (1995)), in which the response time can be greatly improved, thereby permitting results which can be measured within seconds (Barker et al., *Anal. Chem.* 70:971 (1998)).

In the present invention, sol-gel transition can be induced by coagulation, thereby completely obviating the need for any alcohol in the protein encapsulation process when an aqueous silica sol is used as the starting solution. On the other hand, it is also known that when proteins are mixed with colloidal particles, including silica colloidal particles, interactions between them can result in protein adsorption on the particle surface (Haynes and Norde, *Colloids and Surfaces* B2:517–566 (1994)). Upon adsorption, proteins usually lose part of their biological activity due to structural rearrangement. Therefore, the feasibility of using colloidal particles for biomolecule encapsulation was not known, nor would it have been assumed by those in the art, until demonstrated by the present invention.

For efficient use of encapsulated proteins, their concentration is typically kept low compared to the weight or volume of the host matrices. It is known, however, that the protein absorption on colloidal silica particles, and the resultant conformational change is the greatest when the protein concentration is the lowest. Furthermore, for the same weight percent of the colloidal particles used, the resultant conformation changes in the encapsulated biomaterial increases as the colloidal particle size decreases. For example, a number of protein adsorption studies have indicated that hemoglobin undergoes a conformational change while interacting with ultrafine (e.g., diameter=15 nm) silica particles (Kondo and Mihara, 1996; Kondo and Fukuda, *J. Colloid Interf. Sci.* 198:34–41 (1998)). They reported that the extent of conformational change was enhanced by decreasing solution pH, and observed that the conformational change was the largest when the amount of hemoglobin addition was the smallest.

The observed spectral shift in these studies was relatively large, 3–7 nm, indicating strong adsorption of protein onto the oxide surface forming covalent bonds, resulting in denaturation of the biomolecule. Therefore, the feasibility of using colloidal particles, especially using very fine particles of a high concentration, for biomolecule encapsulation was not foreseen, and such practices would have been taught away from, until it was proven by the present invention.

The effectiveness of protein encapsulation using the present alcohol-free, aqueous colloidal sol-gel process, is demonstrated through the use of four diverse proteins—cytochrome c, catalase, myoglobin, and hemoglobin. These proteins were selected as representative models, but are in no way intended to limit the capabilities of the present invention.

Functionally, the representative proteins range from oxygen transporters to catalysts. Each possesses an iron atom present in the central heme group and has well defined optical characteristics in the UV-visible region. Hemoglobin has a globular structure with dimensions of 6.2×5.4×5.2 nm$^3$ (Kondo and Mihara, *J. Colloid Interf. Sci.* 177:214–221 (1996)). The heme group in the hemoglobin allows the protein to carry and store oxygen. In addition, this heme group gives the protein a red color and a distinct spectral absorption band (Soret band) at a wavelength of 406 nm, which allows direct spectroscopic characterization. Hemoglobin is a biomolecule having substantial structural flexibility, but it is also more susceptible to environmental changes (Gekkol et al., *Biochemistry* 25:6563 (1986)); Myer and Pande, p. 179 in *The Porphyrins* (D. Dolphin ed.), vol.3, 1979).

More importantly, each heme group bonds only to specific prosthetic units leading to different biological activities for different proteins (Branden and Tooze, in *Introduction to Protein Structure*, Garland Publishing, Inc., New York, 1991). For myoglobin and hemoglobin, an oxygen atom can bond directly to the iron atom within the heme group, and hence both proteins allow oxygen transport and storage. For cytochrome c, a protein in the terminal oxidation chain in the mitochondria of all aerobic organisms, the heme group is a reversible carrier of electrons, rather than of oxygen. For catalase, the same heme group has yet another function, that of catalysis or enzymatic activity. Thus, each selected protein offers special biomedical and biochemical significance, providing evidence that the present invention is effective with a wide and diverse range of active proteins, including enzymes, without limitation.

Heme proteins are, the most commonly used models for experiments involving absorption measurements, as described herein. However, other proteins and biomolecules are known in the art, and are known to undergo reactions that are measurable, by other techniques. Thus, although heme proteins are utilized in the representative models of the present invention, embodiments of the invention need not be so limited. Use of heme proteins in the exemplified embodiments of the present invention were used for convenience of signal detection.

The strong dependence of gelation kinetics on processing variables and composition, provide significant information in terms of colloidal chemistry, contributing to the effectiveness of the present invention over the prior art in terms of optimized protein stability. The fundamental difference in encapsulating biomolecules between the aqueous and the alkoxide-based processes is that for the present alcohol-free, aqueous, colloidal sol-gel process, biomolecule-solid interactions, e.g. adsorption, take place at the time of initial contact and ends when the biomolecule is completely immobilized. Conditions that minimize the time during which absorption progresses thus contribute to the successful retention of the conformation and the functionality of biomolecules. Information provided by this invention can be used to optimize these conditions.

In contrast to the conditions described as part of the conventional alkoxide methods, the mixing conditions of the present invention are preferably gentle (as opposed to intense, ultrasonic, or the like). This is because many proteins can be denatured under high-sheared mixing. On the other hand, prior to addition of the biomaterial, the aqueous ceramic sol may contain silica (a ceramic oxide) or other ceramic oxide particles ($TiO_2$ for example.), which can be mixed with intensity, e.g., by ultrasound, if needed. If commercial sols are used, of course, no additional mixing is required.

In the metal alkoxide-based process, interactions between the biomolecules and the solvent molecules and/or inorganic monomers, such as tetramethyl orthosilicate, are possible as they are mixed together during synthesis. Interaction either with the solvents, such as alcohol or methanol, or with the inorganic monomers, results in, or causes different degrees of denaturation of the biomolecules. Consequently, since at least some interaction of the biomolecules with the surrounding alcohol molecules in the alkoxide-based process seems inevitable, the damaging effects are particularly critical for some proteins with poor structural stability, such as hemoglobin and catalase.

Fortunately, the deleterious effects of alcohol-contact can be avoided entirely when the present aqueous colloidal process is used, and the conformational change due to the biomolecule: solid interaction are minimized by optimized processing (Liu and Chen, *Acta Materialia* 47[18]:4533–4544 (1999); and presented at the 101 Annual Mtg. of the American Ceramic Soc., Indianapolis, Ind., 1999).

In a preferred embodiment of the present invention, the process is optimized by increasing the gelation rate and drying rate. A high solid fraction of colloidal silica increases gelation rate because of the higher collision probabilities between particles leading to coagulation. A lowered pH has the same effect, because the colloidal particles, e.g., $SiO_2$, are less negatively charged at, e.g., pH 6.2, than at pH 8.2. The isoelectric point of silica is ~pH 2.0. Accordingly, less negatively charged particles have a lower potential barrier against collision, hence a shorter gelation time. These trends can be seen, generally, in the results presented in, e.g., FIGS. 5 and 7.

Additional effects of protein concentration are also due to colloidal chemical conditions. The fact that proteins frequently contain many charged groups may affect the electrolytic properties of the solution. At a higher pH (e.g., pH 8.2, as in FIG. 8), proteins are likely to be fully negatively charged, as are the silica particles, resulting in a monotonic increase of gelation time. At a lower pH (eg., pH 7.2 as in FIGS. 5 and 7), which approximates the isoelectric point of the protein, the extent of charge dissociation on the protein becomes concentration-dependent. Although not wishing to be bound by any particular theory, presumably, this causes the resulting non-monotonic variation of gelation time.

The observed importance of gelation time and drying time suggests that there remains a risk of continued conformational changes for proteins that are suspended in a deformable colloid, and even in a gel. However, as proven by the present findings, this risk can be minimized by shortening the gelation time and the drying time. Once gelation occurs, there is no translational degree of freedom left in the gel. Thus, protein collision and aggregation cannot occur, and the rate of denaturation slows drastically.

Another method for optimizing the process is by controlling the gel microstructure so that the encapsulated biomaterial is permitted only a restricted space, which is not sufficient for extensive conformational change to occur. Variations in the concentration and the size of the colloidal particles used to prepare gels will affect the resulting microstructures. In a homogeneous gel, the particle spacing is proportional to the particle diameter and inversely proportional to the one-third power of the particle concentration. Therefore, by using colloidal particles which range in size from several nm to several tens of nm, especially at high concentrations, nanoscale microstructures can be obtained for the gel which correspond to the encapsulated biomaterial. For proteins, the typical size is of the order of 5–15 nm. For other biopolymers such as DNA, the persistent length is typically of the order of several nm and the radius of gyration is. typically several tens of nm (Fletterick et al., *Molecular Structure: Macromolecules in Three Dimensions*, Blackwell Scientific, Oxford (1985)). Thus, the various size scales in the gel and biopolymers span a range that will affect conformation, structure, and activity of biomolecules.

The use of two or more different particle sizes is also encompassed within the present invention. On one hand, large particles can be used for space filling to accelerate gelation, while having a relatively small effect on particle spacing (since their number density is low but their volume fraction is high), and hence the effect on the biomolecule is also low. On the other hand, a depletion force can be found that is proportional to the size ratio of the large and small particles and to the concentration of the small particles (Asakura el al., *J. Chem. Phys.* 22:1255 (1954); Vrij, *Pure and App Chem.* 48:471 (1976); Attard et al., *J. Chem. Phys.* 92:4960 (1990)).

This force results in the aggregation or crystallization of the large particles. Thus, it is possible to manipulate these parameters (particle size, size distributions, and number concentrations) to obtain various microstructures in these inorganic/organic compositions to exhibit different properties.

The pores can be developed and controlled by packing (upon gelation) of colloidal particles of different size, and the pore size can be strongly related to the starting size of the colloidal particles (Iler in *The Chemistry of Silica*, Wiley, New York, 1979; and by Shafer et al., *J. App. Phys.* 61[12]:5438–5446 (1987)). This may be difficult by means of the alkoxide-based sol-gel process, but is easy to achieve via the aqueous colloidal process, under a constant value of solution pH.

In the present invention, pore size can be varied from 1 to 100 nm or more to accommodate biomolecules and cells of different sizes. The preferred size ranges from 2 to 50 nm. However, the pore size is generally dependent on the size of biomaterial to be encapsulated. For example, if proteins are to be encapsulated, the more preferred pore size will range from a few to several tens of nanometers. For DNA, it is of the order of 15 to 30 nm. For cells, the pore size may be even larger, ranging from 100 nm and above. Also, since permeativity is dependent on pore size, it can also be varied over a broad range in the colloidal sol-gel process to affect the reaction kinetics of the resultant composites.

The biomaterial of the present invention can be used in a partially or completely dry state, depending on time available and the application. However, the encapsulated material within a completely dry gel provides the most consistent results and remains more stable, i.e., maintains a longer shelf life. Tests have proven that stability of the biomaterial within the dried product is maintained for months of storage, and indicate that reliable storage will be possible for years.

The properties of the dried gels prepared in accordance with the present invention indicate that the highly porous structure of the matrix comprises very small diameter interconnecting channels. If the channels were not very small, at least some portion of the encapsulated biomaterial would elute from the matrix, which it does not. If an extensive interconnecting network of channels did not exist, the test substance would not evenly reach the encapsulated bioactive material, thus exhibiting what would appear to be a decrease in the activity of the biomaterial, which has not been observed. In addition, the dimensions of each channel in the porous network must be very small, not exceeding about 0.4–0.5 microns, or the optical transparency of the glass-like nanocomposite would be compromised.

For example, assuming that encapsulated proteins are individually trapped in isolated cages within the colloidal particle network, the size of such a cage in a preferred embodiment of the present invention can be estimated using the measured pore size (diameter ~5.3 nm) of the dried gel containing hemoglobin, and correcting for volume shrinkage (assuming 62%) during drying. This estimate places the average size of the initially-developed network cage at 7.2 nm, which is somewhat larger than the molecular size of hemoglobin. Therefore, there remains some freedom for the entrapped molecule to undergo a slow and limited conformational change, equivalent to unfolding in a fresh gel. This continues during drying until the cage shrinks to a size that completely "freezes" the molecule. Thus, without being bound by a particular theory, this principle explains why a slow degradation of relative absorbance is seen during drying, as shown in the 1 nm change from fresh in FIG. 4.

Shrinkage during drying eventually causes the cage to contract to a smaller size (diameter ~5.3 nm), which is then of the molecular size of hemoglobin. Therefore, after drying, the protein is completely frozen, and further degradation of its properties is avoided. The dimensional restrictions of the dried matrix act as an effective stabilizer, thereby keeping the protein from denaturation or further conformational change, even during long-term storage. Thus, structural confinement becomes advantageous for retaining the stability of the entrapped biomolecules.

In the present invention, aqueous colloidal silica sots with an average particle size ranging from 3 nm to 21 nm were employed in order to prepare gels of different pore sizes. The preferred particle size produces in the dried gel a final average pore size smaller than, or of about the same size as, the biomolecule to be encapsulated. For example, for the encapsulation of the representative proteins used to demonstrate the preferred embodiment, the preferred particle size ranges from 1 to 10 nm, to produce a pore size ranging from 2 nm to 15 nm. For the encapsulation of hemoglobin, the more preferred particle size would be 4–7 nm, to produce a final pore size of about 5 mn.

A clear transition from no-denaturation to denaturation is seen when the pore size crosses over (exceeds) the size of the protein. For hemoglobin, this crossover occurs when the starting particle size is greater than about 7 to 8 nm.

The pH of the sols is adjusted using HCl and/or $NH_4OH$. The preferred pH ranges from about 5 to about 9, with the particularly preferred pH ranging from 6 to 8. For the preferred embodiment of the present invention, as exemplified using hemoglobin, the more preferred pH is in the physiologically compatible range of about 5.5 or 6 to about 8, and is most preferred at about pH 6.2–7.2.

Most biopolymers (and water-soluble polymers in general), including proteins, are polyelectrolytes containing charge groups, wherein it is energetically favorable to form covalent bonds with the charge groups on the oxide surface (Norde et al., Colloids and Surfaces 64:87 (1992)). Therefore, when proteins are free to adsorb onto the oxide surfaces, as in prior, classical adsorption studies, they have a strong tendency to be adsorbed, and form covalent bonds with the oxide particles. (Norde, 1995; Haynes et al., J. Colloid and Interface Sci. 169:313–328 (1995); Malmsten et al, J. Colloid and Interface Sci. 207:186–199 (1998)). This, in turn, causes unfolding of the primary, secondary and tertiary structures of proteins, and hence, their denaturation. The tendency to adsorb increases with the ratio of surface area of oxide particles.

At the same weight concentration of particles, the total surface area increases with decreasing particle size. On the other hand, if the concentration of proteins is high, there is competition among proteins for the available surface area, and the available surface area must be shared by several biomolecules. Therefore, complete adsorption in the unfolded state is not possible. This explains why proteins absorb strongly to nanometer-sized particles, and why the resultant denaturation is less severe if the amount of protein in the solution is higher (Kondo et al., J. Colloid and Interface Sci. 177:214–221 (1996); Kondo et al., 1996; Kondo et al., 1998).

In the present invention, particle surface coverage is very low, e.g., <0.1% during encapsulation, and because of the very small morphological length scales, the surface area of the oxide surfaces is exceedingly large. However, denaturation is avoided, contrary to the results of the prior art. This may be explained by the small pore size between highly concentrated colloidal particles used in our invention.

According to kinetic studies, although not wishing to be so bound, it further appears that when the cage size is sufficiently small as to fully constrain the entrapped protein molecule, no further conformational change can occur in the biomolecule. Therefore, trapped in such a cage, a protein molecule can have, at most, a few charge groups covalently bonded to the surrounding oxide surfaces. This minimal bonding appears to be insufficient to cause the large conformational changes required for unfolding or disrupting the tertiary structure of the protein, of the type that can most critically affect the heme group responsible for the characteristic absorption.

Before gelation occurs, the space between the particles is not rigid, and the biomolecules can have some freedom to conformationally change. However, this flexibility is greatly reduced upon gelation, and is completely removed after drying (which shrinks the cage size to that of the biomolecule). Therefore, a rapid gelation and post-gelation shrinkage that further reduces the cage size are beneficial to retention of conformational stability. This leads to the observed effect of pH and the selection of the solid fraction on the gelation kinetics.

Figure 14:
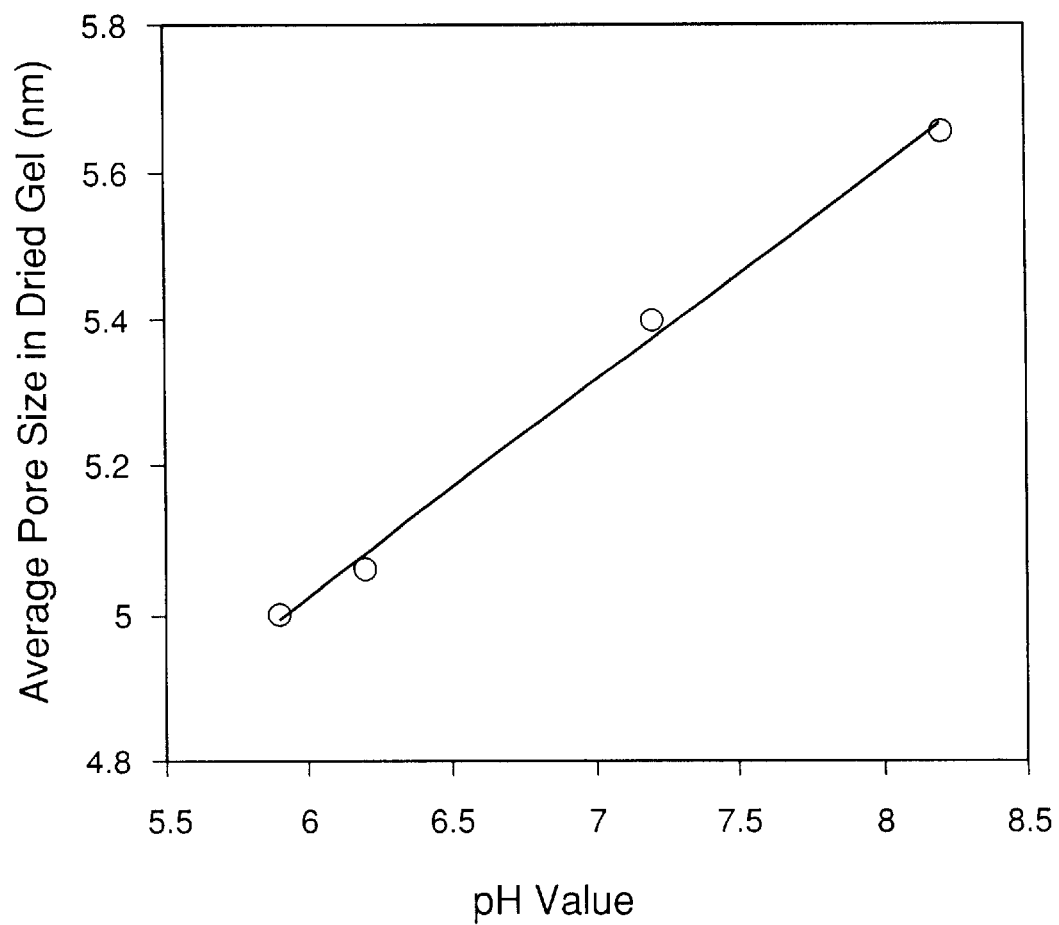
FIG. 14 depicts the average pore size of the dried silica gel prepared under different pH values.

When pore-size measurements were performed for dried gels, which had been prepared at different pH levels, as shown in FIG. 14, the average pore size was seen to increase from 5.06 nm at pH 6.2 to 5.65 nm at pH 8.2. Previous estimates of pore size for colloidal silica, e.g., by Iler in The Chemistry of Silica, Wiley, New York, 1979; and by Shafer et al. J. App. Phys. 61[12]:5438–5446 (1987)) suggested that the coordination was between 4 to 6 nm in the early stage of network formation. Thus, the pore size data are consistent with the well-known geometry of particle packing that shows the void space increases with the coordination number (Avery and Ramsey, J. Colloid Interf. Sci. 42[3]:597–606 (1973)).

Accordingly, the present invention demonstrates that a lower pH and a higher solid fraction in the matrix (relative to a fixed amount of proteins) reduces the gelation time and the pore size. Hence, the combined elements have proven beneficial for the conformational stability of the encapsulated biomolecules.

The gels appeared transparent in color for a colloid size of 7 nm to 12 nm, but become somewhat less transparent as the colloidal size approaches 20 nm or more. Studies by Kondo et al., 1996, 1998 reported a similar resolution when monitoring the conformational change of hemoglobin as compared to that observed by circular dichromism (CD). Thus, the preferred colloidal particle size used in the present invention when optical or colorimetric detection or measurements are employed, is less than 20 nm in diameter; the more preferred size is less than 18 nm; and the most preferred size is less than 10 nm. Although colloidal particles sizes larger than 20 nm, will still function in the present invention, optimal performance is obtained when the encapsulated material is proteinaceous if the particles are less than 20 nm. On the other hand, if the encapsulated material is very large, e.g., DNA or a cell, then particles sizes much larger than 20 nm would be preferred.

During the drying process, the gel shrinks in size, which results in a volume decrease to about 10–50% of its original wet state volume. Based upon the initial quantity of solids in the composition, the calculated pore volume of the dried product is ftom about 20% to 80% that of the initial wet gel.

In order to estimate the pore size at the gelation stage, where the pores are filled with water, the gels were dried at 4° C., and the volume shrinkage of the gel (termed an "aged gel"), was recorded. The resulting pore size ($\Delta_d$) in the dried gel was then determined using BET(Brunauer, Emmett, Teller) (nitrogen) sorption technique. The pore size ($\Delta_d$) in the gelation stage ($\Delta_g$) was then estimated by formula 1:

$$\Delta g = \frac{\Delta d}{(1-V)^{\frac{1}{3}}} \quad (1)$$

where V is the total volume shrinkage of the gel after drying. For example, the shrinkage is calculated to be 62% for 7 nm colloid sols forming the sol-gel, 54% for 12 nm particles and 50% for 21 nm particles.

As expected, gels with a smaller pore structure can be obtained through the use of smaller colloidal particles. Both the measured $\Delta_d$ and the calculated Ag are proportional to the colloidal size.

In the aged wet gels, the corresponding pore size is thus estimated to be about 6.9 nm for the smallest particles, which is close to the equivalent diameter of hemoglobin, i.e., 7 nm. Larger pores, 11.6 nm and 19 nm, were developed in the aged gel for colloids of 12-nm and 21-nm diameter, respectively. Even after drying, these large pores are still much larger than the size of hemoglobin. This explains the much better protein stability attained when the gel is made of smaller sized colloids, which have been selected to produce pores, when dry, of approximately the same size as the biomaterial being encapsulated.

The surface properties of the colloidal particles and their interactions with the biomolecules are important for the preparation and application of the sol-gel composites containing encapsulated biomolecules. These properties are sensitive to the electrochemical conditions of the solution (pH, electrolytes, and composition), as well as the presence of functional groups, polymers, and monomers that may participate in competitive absorption, polymerization, gelation, and crosslinking. The isoelectric points of many colloidal oxide particles and biomolecules are known. This knowledge can be used to tailor the surface activity, adsorption kinetics, and colloidal behavior of oxide-particle/biomolecule solution.

Functional groups of various kinds can also be used to vary the surface properties of the oxide particles and of the gels. For example, introducing functional groups of long alkyl chains can systematically change hydrophobicity. Water-soluble polymers and associated monomers, when incorporated into the gel, can dramatically modify its hardness, ductility, and viscoelastic responses. Nevertheless, each behaves in accordance with known laws and principles, permitting one of ordinary skill in the art to modify the inorganic components of the matrices or the biomaterials or the conditions under which they are combined, in accordance with the present invention to optimize and predict the performance of the resulting product as a sensor or the like without undue experimentation.

In addition to colloidal silica, other oxide particles may be introduced to form the backbone of the gel. For simplicity, it is advantageous to use mono-sized spherical particles, which will follow the principles of homogeneous precipitation. Other known colloidal particles can be readily utilized in accordance with the present method, including, but not limited to $TiO_2$, $Y_2O_3$, $Al_2O_3$, $TiO_2$, $SnO_2$, $ZrO_2$, MgO, $Nb_2O_5$, ZnO and $CeO_2$. Each inorganic host offers certain unique and different optical, electrical, and surface properties to the matrix, which can be selected based upon the intended purpose of the resulting product.

The nature of each particle will affect the kinetics of gelation, the microstructure of the gels, as well as the interaction between the organic, encapsulated biomaterial and the inorganic surfaces in the matrix. However, since each behaves according to known scientific principles, the alternate colloidal particles can be readily substituted without extensive experimentation by one of ordinary skill in the art. Moreover, for certain applications, causing alternative characteristics in the gel may be advantageous.

When pH values are kept relatively neutral, as is required for the survival of many biopolymers, the surface of the oxide particles is either acidic, neutral, or basic, depending on their respective isoelectric points. They will thus adsorb biopolymers in essentially different ways. Therefore, by varying the particle types (e.g., $SiO_2$, $TiO_2$, $Y_2O_3$, $CeO_2$, and the like), freedom is gained to tailor surface properties of the colloidal particles, which in turn have a profound influence on the adsorption behavior and the conformation of biomolecules in the space between particles in the gel matrix.

The encapsulated biomolecules prepared in accordance with the methods of the present invention demonstrate much greater temperature and environmental stability over comparable control biomolecules maintained in any physiologically compatible fluid, or in simulated fluids, such as phosphate buffer solution (PBS). For example, while hemoglobin stored simply in PBS denatures at temperatures above 50° C., the same material when encapsulated in a silica matrix as described herein, shows no deterioration, even at temperatures as high as 80° C. Similarly, while hemoglobin stored simply in PBS denatures at alkalinity above pH 8, the same material when encapsulated shows no deterioration, even if the pH is raised to pH 11.

Other suitable biological buffers are, but not limited to, sodium acetate solution, sodium bicarbonate solution, sulfonic acid solution, aminomethane, aminomethane, methyglycine.

The preparation temperature of the present invention can range from body temperature (about 37° C.) and below. Higher temperatures are less optimal, and encourage degradation; whereas, lower temperatures are preferred, and slow degradation. Preferably, the temperature ranges from room temperature and below, to as low as 4° C. Optimally, the temperature is maintained close to 4° C. to control degradation to the greatest extent possible. However, it is recognized that the technicians working in the field operate more efficiently at room temperature, and drying takes longer at low temperatures.

Lower humidity is also preferred in the practice of the present invention, particularly during the gel drying stage, so long as the humidity is not so low as to cause cracking. Drying takes longer at high humidity.

Gelation additives are beneficial to certain embodiments of the invention. For example, acidified $Na_2SiO_3$ is a gelation additive. Other organic, water-soluble polymers or soluble salts, such as silicate salts, can also be used. In some instances, hydrophobic coating has proven useful.

When the encapsulated biological material is a protein, one or more organic additives may prove beneficial. For example, the addition of polyethelene glycol (PEG), at from 1 to 10 wt % will further stabilize the protein molecules.

More importantly, in accordance with the present invention, the encapsulated biological materials were shown to maintain high activities. For example, catalase-containing silica gels, when sufficiently dispersed to avoid diffusion from the encapsulating matrix, maintains the same capability for generating oxygen, i.e., the same level of activity, as the same molecule stored simply in PBS. Consequently, in accordance with the present invention, encapsulated biomolecules can survive storage or use under significantly harsher conditions than the physiologically acceptable environment of a normal living body.

This attribute is an important advantage in biotechnology, since many biomolecules are enzymatic in nature and their bioactivities can be greatly enhanced if the process temperature is raised. Of course, in addition, the enhanced stability of the encapsulated biomolecules of the present invention offers significant advantages for their storage, transportation, or handling, in either clinical, field or industrial procedures.

In addition, the encapsulated biomaterials may be recoverable. Studies have indicated that lipases have been encapsulated, and then recovered from the biomatrix, and reused. Even if the protein is not reclaimed per se in its free form, the beads of glass-like material containing the encapsulated protein are large enough to be capable of physical separation from, e.g., the reactants and the medium. Thus, after separation, the "encapsulated" biomaterials can be reused. Tests have shown that such proteins can remain active and reusable for as many as 1000 hours of reaction time, further demonstrating the stability of the encapsulated materials.

In sum, encapsulation of biological molecules, such as proteins and enzymes, into a porous inorganic matrix is particularly useful, so long as the entrapped biomolecules retain a substantial level of activity and functionality, and the matrix pores allow the diffusion of reactant molecules through interconnecting channels, permitting reactions to occur in the entrapped biomolecules. The present invention is further described in the following examples. These examples are not to be construed as limiting the scope of the appended claims.

In the following examples, using known techniques, gelation kinetics can be monitored routinely by the measurement of viscosity. Microstructure can be characterized using BET, transmission electron microscopy, small angle X-ray and neutron scattering. Such techniques are used to define the pore size, pore distribution, connectivity of the pore space, and agglomeration of colloidal particles. Biopolymer structures are probed using absorption spectra over visible and UV ranges (Havel, *Spectroscopic Methods for Determining Protein Structure in Solution*, VCH Publishers, Cambridge (1996); Demchenko, *Ultraviolet Spectroscopy of Proteins*, Springer-Verlag, Berlin (1986)), static and dynamic light scattering, small angle scattering, differential thermal ananlysis. Using absorption spectra, the reaction of these composites with reagents can also be monitored, since color changes are manifest with many such reactions. Relaxation properties of the polymer can be probed using differential thermal analysis, depolarization current and dielectric measurement, to take advantage of the polar character of the biopolymers. The adhesion properties between biopolymers and oxide particles can be examined using conventional mechanical testing such as tensile/bend strength test followed by electron microscopy.

EXAMPLES

Procedure and Methods

FIG. 1 depicts a flow chart of the synthesis scheme for encapsulating biological materials via the present aqueous, colloidal sol-gel process. More specifically, as applied in the following examples, wherein the gel is a silica gel, Part A (the sol) was formed from 1.5–3 ml of a commercially-available colloidal ceramic oxide sol, preferably silica sol (e.g., Ludox SM-30, spherical particles with an average diameter of 7 nm; specific surface area of 360 m$^2$/g) at ~pH 10.3. Part B (the sodium silicate solution) was prepared by adding 0.01 mole of reagent-grade $Na_2SiO_3$ in distilled water, then acidified until completely dissolved by adding concentrated HCl (1.6 N), resulting in a final silicate solution (which is no longer in the oxide form) having a pH value <1.0.

To form the gel, Part A (the silica sol) and Part B (the silicate solution) were mixed in a 20 ml glass tube in the appropriate amounts (a lot of Part A, specifically 1.5–3 ml of prepared sol, and a small amount of Part B, specifically 0.06–0.1 ml of acidified 0.1 M sodium silicate ($Na_2SiO_3$) solution), until together the two parts reached a selected pH of 6.2 to 8.2. In this reaction, Part B acts as the polymerizing agent, that undergoes hydrolysis and condensation, causing the ceramic particles in A to gel by forming bridges and interconnecting channels between particles.

When the gelation additive, in this case $Na_2SiO_3$ is acidified in aqueous solution, it forms the free ion, $Na^+$, and $Si(OH)_4$, which is a dissolved hydroxide, resulting in gelation Polymerization occurs via the reaction $nSi(OH)_4 \rightarrow nSiO_2 + 2nH_2O$. Thus, gelation is enhanced because the polymer bridges in the particles have already been initiated. The key to the reaction, therefore, is the presence of $Si(OH)_4$ as a dissolved hydroxide (sometimes called silicic acid). For other ceramics, the equivalent is $Ti(OH)_4$ for $TiO_2$, $Al(OH)_3$ for $Al_2O_3$, and the like.

The final pH of the composition is compatible with the physiological pH of the human body, making it possible, after the solution was prepared, to add a small amount (1.5 ml) of protein in phosphate buffer solution at a concentration ranging from 300 mg/ml to 1600 mg/ml. As a control, 0.01 M phosphate buffer solution (PBS, pH from 6.2 to 8.2), but without the protein, was mixed with an identical amount of the colloidal suspension (solid concentration of is 16 vol%) having the same pH value. The ionic strength of all final solutions was adjusted to 0.05 M using regent-grade NaCl (Aldrich Chemical, USA).

The prepared protein-containing gel solution assumed a visible color, which was characteristic for each incorporated protein. The solution was then gently shaken until it became viscous, after which it was quickly shaped, and gelation occurred. A transparent, solid-like, protein-containing gel (herein referred to as an "aqueous silica gel") was ultimately formed. The final protein concentration in the aqueous silica mixture was 20 μM. The gel was then aged (an "aged gel") and dried slowly at a temperature of ~4° C. over a period of 2–4 weeks (a "dried gel").

The encapsulated proteins used in the following examples were bovine heart cytochrome c, bovine liver catalase, horse muscle myoglobin, and bovine hemoglobin (all Sigma Chemicals, USA). Table 1 sets forth some important parameters and biological functions of these proteins.

TABLE 1

Representative biomolecules and their molecular parameters.

| Bio-molecule | Molecular Weight | Dimensions(nm$^3$) | Compressibility ($10^{12}$ βs)* | pH$_{iep}$ | Function |
|---|---|---|---|---|---|
| Cytochrome c | 12,327 | 2.5 × 2.5 × 3.7 | 0.066 | 10.6 | Redox |
| Myoglobin | 17,800 | 4.4 × 4.4 × 2.5 | 8.98 | 8.2 | $O_2$ transporter |
| Hemoglobin | 64,550 | 6.4 × 5.5 × 5.0 | 10.9 | ~7.0 | $O_2$ transporter |
| Catalase | 60,000 | 5.2** | NA | NA | Enzymatic catalyst |

*See, Tanford in Physical Chemistry of Macromolecules, Table 21.1, John Wiley & Sons, 1961.
**See, Gekkol and Hasegawa, Biochemistry 25:6563 (1986).

Notably, a higher value of adiabatic compressibility indicates greater flexibility in the protein, i.e., the proteins were found to be more susceptible to conformational change or denaturation. Therefore, hemoglobin, the protein with the lowest conformational stability and the greatest flexibility of the representative biomolecules, was selected as the model protein for further investigation of process optimization. Hemoglobin has a globular structure (Perutz, *Brit. Med Bull.* 32:195–208 (1976)), with dimensions (6.4×5.5×5.0 nm$^3$) comparable to the size of colloidal silica (7 nm).

A UV-Visible spectrophotometer (Beckman, Model DU-600) was used to characterize the conformational change/denaturation of the proteins encapsulated in aqueous colloidal silica matrices. To evaluate whether the interaction between a protein and its surrounding environment led to a conformational change in the tertiary structure (around the heme group) of the protein, change in the absorption spectrum was measured. The characteristic absorption spectrum for cytochrome c was determined to be at wavelength 409 nm; for catalase it is 406 nm; for myoglobin it is 409 nm, and for hemoglobin it is 406 nm.

The gelation kinetics of the protein-silica sol mixture was tracked using a viscometer (Brookfield, Model DV-II). A constant shear rate of 0.6 $sec^{-1}$ (the lowest shear rate attainable for the instrument) was used to monitor the viscosity change of the mixture with time at ambient temperature. The time when the viscosity of the mixture solution reaches the maximum limit of the instrument is defined as "gelation time" (tg).

Example 1
Optical Characteristics of Protein-Doped Aged Gels

Figure 2A:
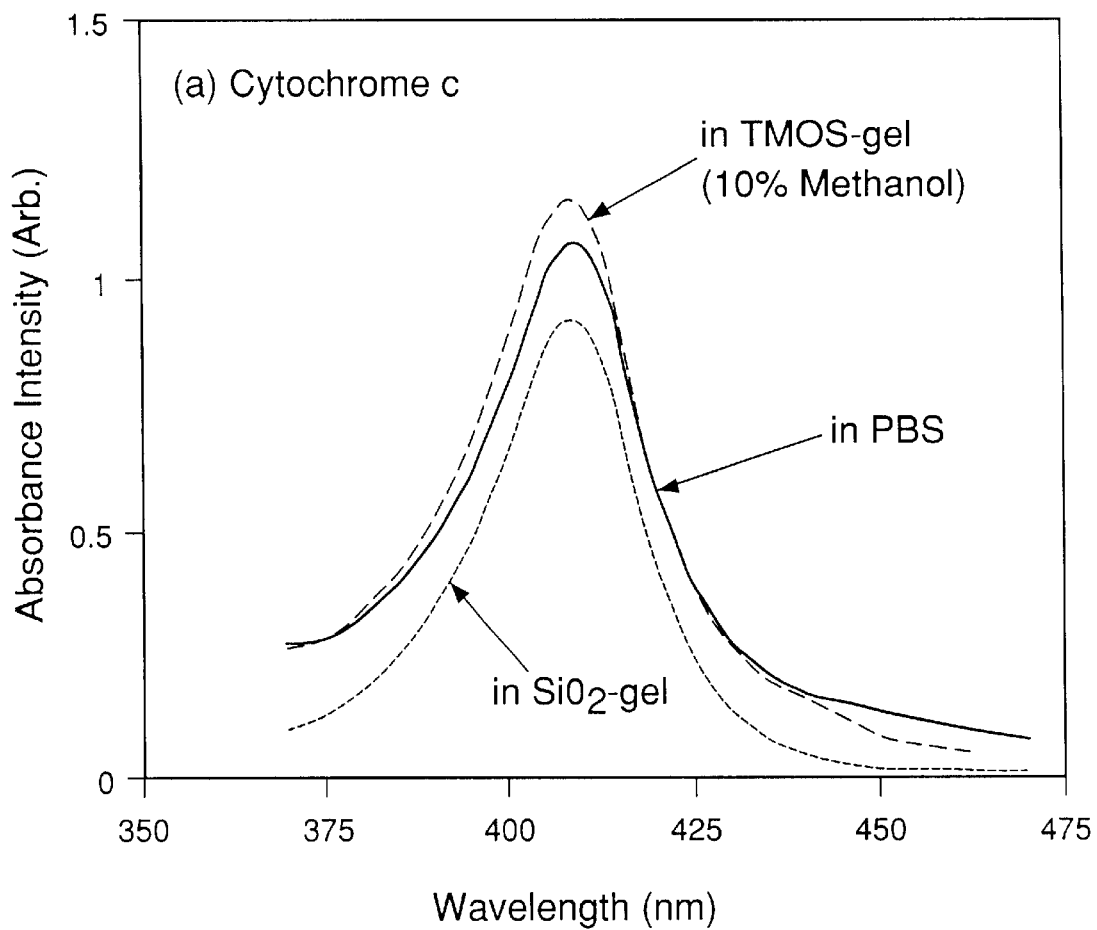
FIGS. 2A and 2B graphically display the absorption spectra of (A) cytochrome c, and (B) myoglobin encapsulated in aqueous silica gel, as compared with encapsulation in TMOS-based gel, together with their spectra for native-state conformations in phosphate buffer solution.
Figure 2B:
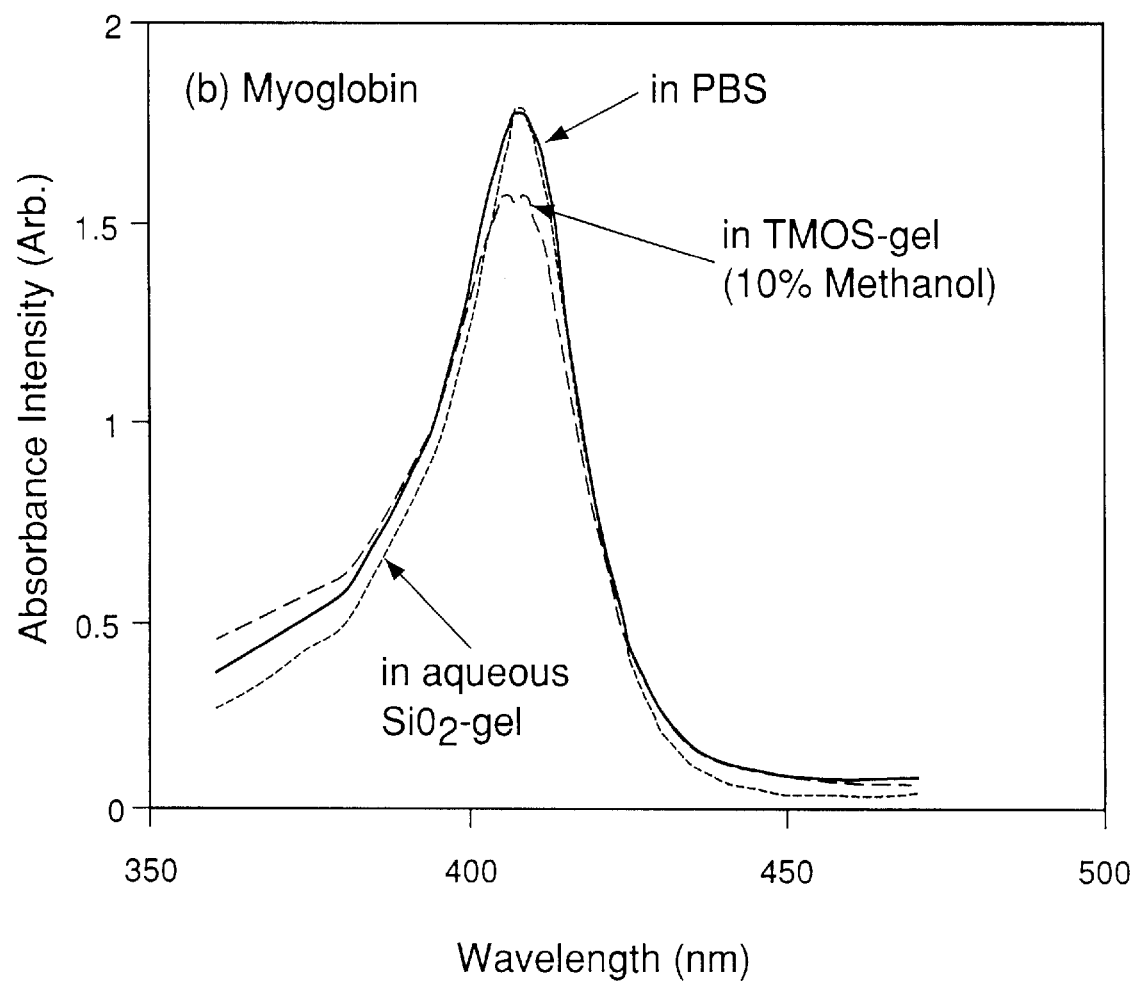

In accordance with the preceding methods, FIGS. 2(*a*) and (*b*) show two examples of the absorption spectra, respectively, of cytochrome c and myoglobin encapsulated in aqueous silica gels. These were in turn compared with the spectra of the same proteins in PBS, and with those encapsulated in TMOS-based silica gels synthesized using the modified sol-gel process proposed by Ellerby et al., 1992. The silica concentration in both types of gels was 8.8 vol %, and a pH of 7.2 was used in their preparation.

The absorption spectra of protein-doped aqueous silica gels generally showed a decrease in absorption intensity. By comparison, comparable biomolecules encapsulated in TMOS-based gel, except in the case of myoglobin, showed an increased absorption intensity. This is consistent with a previous report by Miller et al., 1996, using the same alkoxide-based synthesis scheme.

The absorption spectra of both types of gels also showed a difference in intensity, except for myoglobin, which demonstrated almost identical absorption spectrum to that of the native state in buffer solution. Table 2 depicts the resulting values of relative absorbance (k) of the spectra and the corresponding spectral shift ($\Delta\lambda$) for all four representative proteins encapsulated in the two types of gels.

TABLE 2

Comparison of the spectral shift ($\Delta\lambda$, nm) and relative change of absorbance intensity (k, %) of proteins encapsulated in aqueous silica gels (ASG) and TMOS-based silica gels (TSG).

| Proteins | $\Delta\lambda$ | | K | |
|---|---|---|---|---|
| | ASG | TSG | ASG | TSG |
| Cytochrome-c | −1* | −1 | −14.4** | 12.5 |
| Catalase | 0 | −2 | −34.0 | 41.3 |
| Myoglobin | 0 | −3 | −0.68 | −12.3 |
| Hemoglobin | 0 | −2 | −22.3 | 23.5 |

*"minus" (−) sign means long-wave shift of the spectrum in gel, with reference to that in buffer solution.
**"minus" (−) sign means a decrease in absorbance intensity of the spectrum in gel with reference to that in buffer solution.

Both k and $\Delta\lambda$ were determined based on the characteristic absorption band of the corresponding proteins in buffer solution, relative to those in gels. Obviously, proteins encapsulated in TMOS-based gels exhibited a longwave shift of 1–3 nm, indicating a change in protein conformation (Dunn et al., *Acta Mater.* 46[3]:737–741 (1998)), as was expected from findings in the prior art. These interactions essentially involve van der Waals force and hydrogen bonding, although a detailed understanding of the spectra shift is difficult to obtain because of the diversity of the environmental changes that may have affected the protein conformations during the course of the alkoxide-based sol-gel process.

Figure 3:
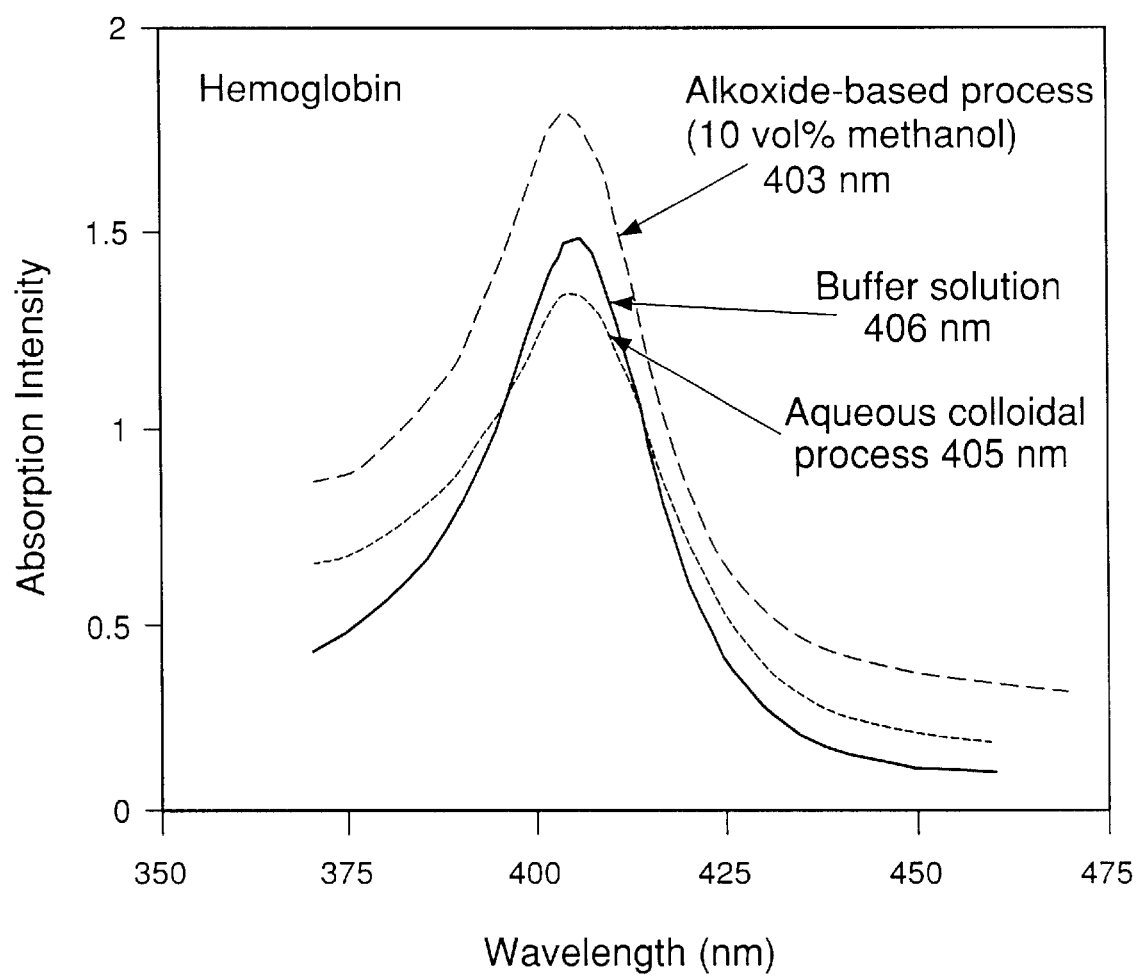
FIG. 3 graphically displays a comparison in the absorption spectra of a protein when stored in a buffer solution as compared with storage in an aged gel. Although no appreciable spectral shift was detected; a decrease in absorbance of ~10% was observed in the protein in the buffer solution, with respect to the native-state conformation of the same protein.

In contrast, there is little or no spectral shift that was observed in doped aqueous silica gels, indicating that the conformation of the encapsulated protein was essentially preserved. As seen in FIG. 3 the absorption spectra of a protein is compared in the buffer solution and in the aged gel. No appreciable spectral shift was detected; however, a decrease in absorbance of ~10% was observed in the protein in the buffer solution, with respect to the native-state conformation of the same protein. This decrease was caused by the interaction, induced by protein-solid adsorption, between the heme group and the tertiary structure of the protein, leading to a change in protein conformation.

For comparison purposes, the absorption spectrum resulting from protein encapsulation by a modified sol-gel process is also given in FIG. 3. As expected, a slightly larger spectral shift (3 nm) was seen in the conventional modified alkoxide process, as compared with the present aqueous colloidal sol-gel process, indicating that alcohol molecules substantially denature the encapsulated protein. In an aqueous environment, interfacial interactions between proteins and colloidal particles are the major factor in determining the protein structure and as such have been a major research objective in the adsorption literature. Such interactions can cause a decrease in absorption intensity which, in the case of hemoglobin, is essentially induced by a weaker interaction between the heme group and the polypeptide chains in the proteins relative to the native state (Kondo and Mihara, 1996). The present spectral observation regarding the heme proteins, all showing a decrease in absorption intensity, is consistent with the reported findings. Therefore, current optical characterization evidences that the use of an aqueous encapsulation route offers a successful approach for protein stabilization, especially for such proteins as myoglobin, hemoglobin, or catalase that have poor conformational stability.

Figure 4:
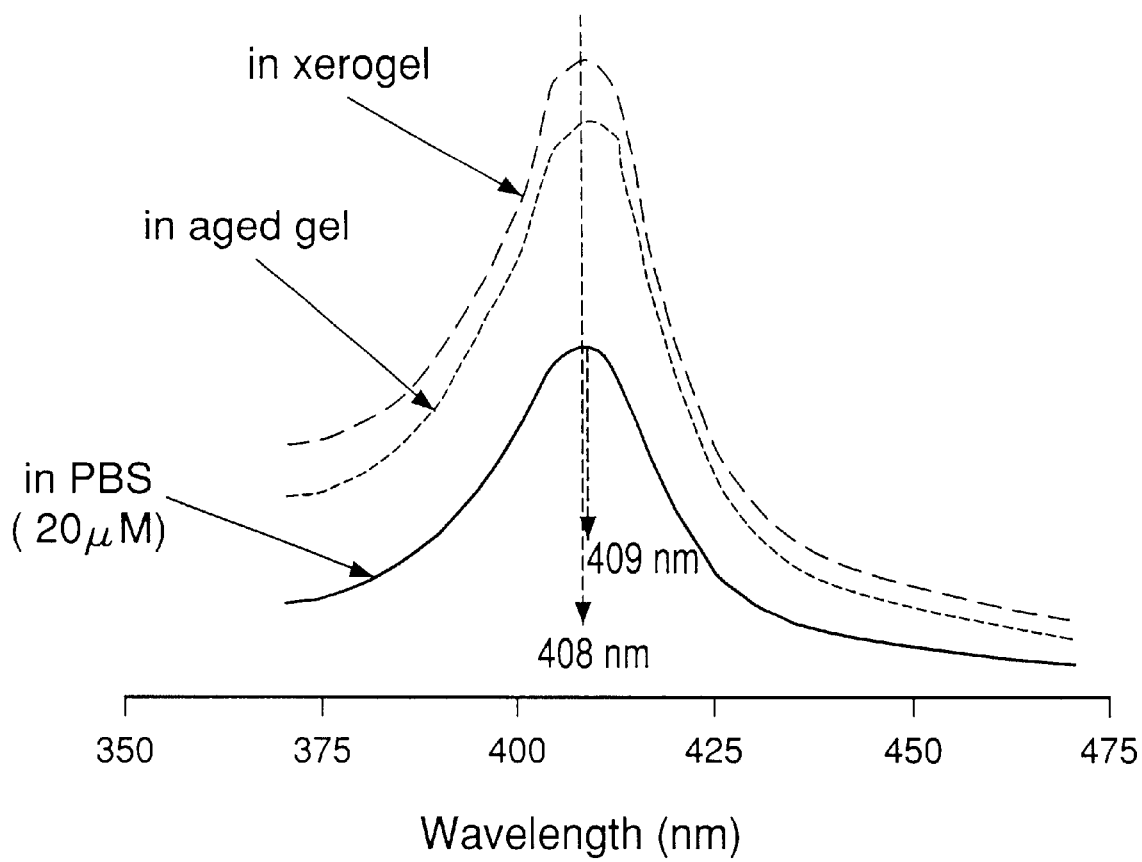
FIG. 4 graphically displays the absorption spectra of cytochrome c after long-term encapsulation in silica gel matrices, showing similar spectral shape and a spectral shift of only 1 nm, when compared to 20 $\mu$M cytochrome c in buffer solution.

In fact, when tested, cytochrome c, which has the best conformational stability among the four representative proteins, appeared to undergo similar, but perhaps less significant, conformational changes in both types of gels. The long-term stability of cytochrome c encapsulated in an aqueous silica matrix was demonstrated by drying for 2 months. The gel remained transparent and the characteristic red color of the cytochrome c was clearly visible. The corresponding absorption spectrum, as shown in FIG. 4, indicates a small spectral shift of 1 nm, relative to that in buffer solution, which was the same as in a fresh gel. Thus, the conformational stability of the protein after long-term encapsulation has been confirmed.

Example 2
The Influence of Synthesis Conditions

Without any alcohol in the current synthesis, in which hemoglobin was the model, the solid concentration and pH of the synthesis were the major issues of interest because both parameters affect not only the kinetics of the sol-gel transition (gelation), but also interactions between hemoglobin and the colloidal particles (Kondo and Mihara, 1996).

A. The Effect of the Silica Solid Fraction

Figure 5:
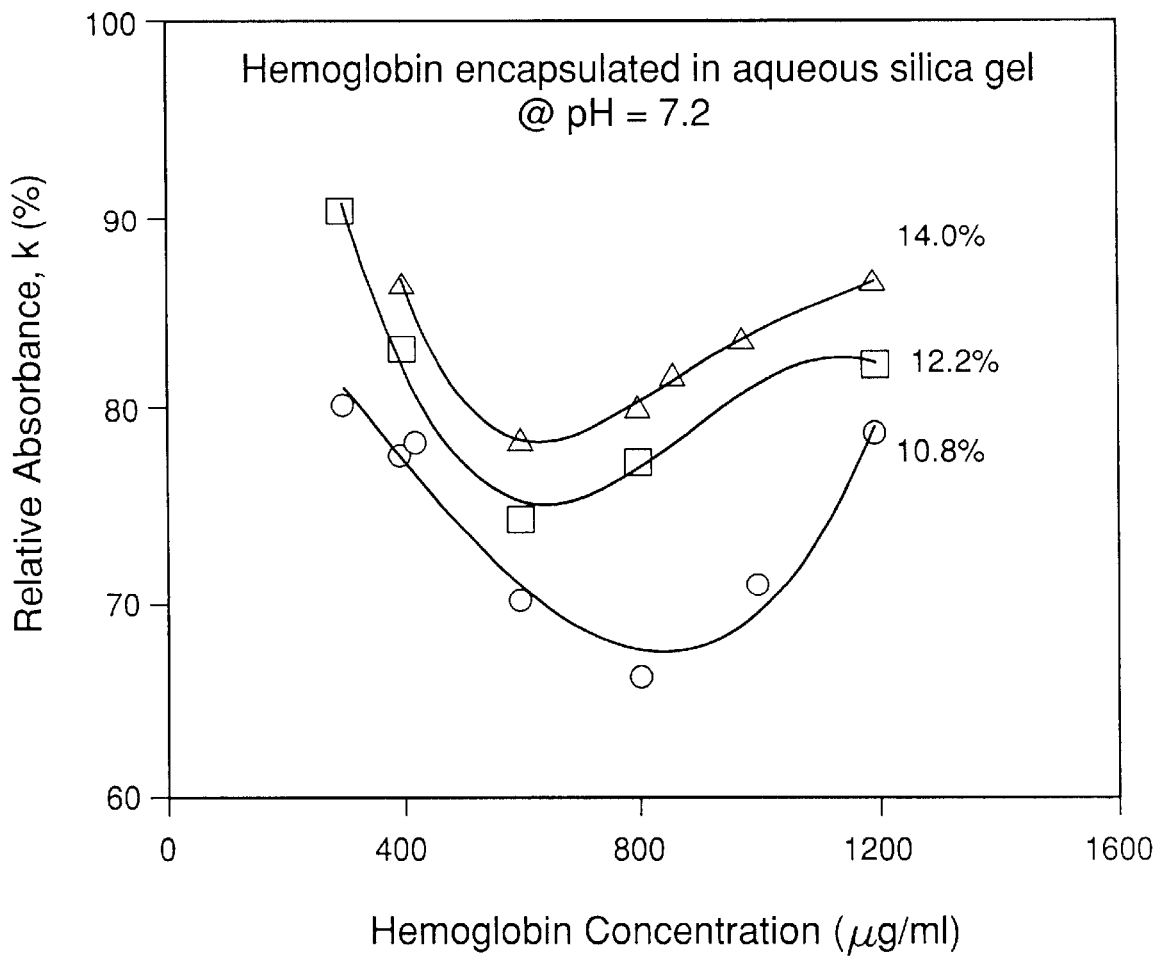
FIG. 5 graphically displays the effect of protein concentration on the relative absorbance of hemoglobin encapsulated in aqueous silica gels at pH 7.2, made from colloidal sols of different solid concentrations. Each curve is labeled with the solid concentration in volume percent.

FIG. 5 shows the effect of silica solid fraction (in vol %) on the relative absorbance of aqueous silica gels doped with various hemoglobin concentrations. The pH value of the protein solution, as well as the colloidal silica, was maintained at a constant at 7.2 in these experiments to avoid other variables. An increase in solid fraction was found to cause the relative absorbance of the encapsulated hemoglobin to increase to levels as high as 90%, from a low of ~65% observed in gels of having lowest solid concentration. All these curves show a U-shape, i.e., for a given solid fraction, the relative absorbance of the protein decreases with initial increase of protein concentration to a minimum and then goes up with further increase in protein concentration.

Figure 6:
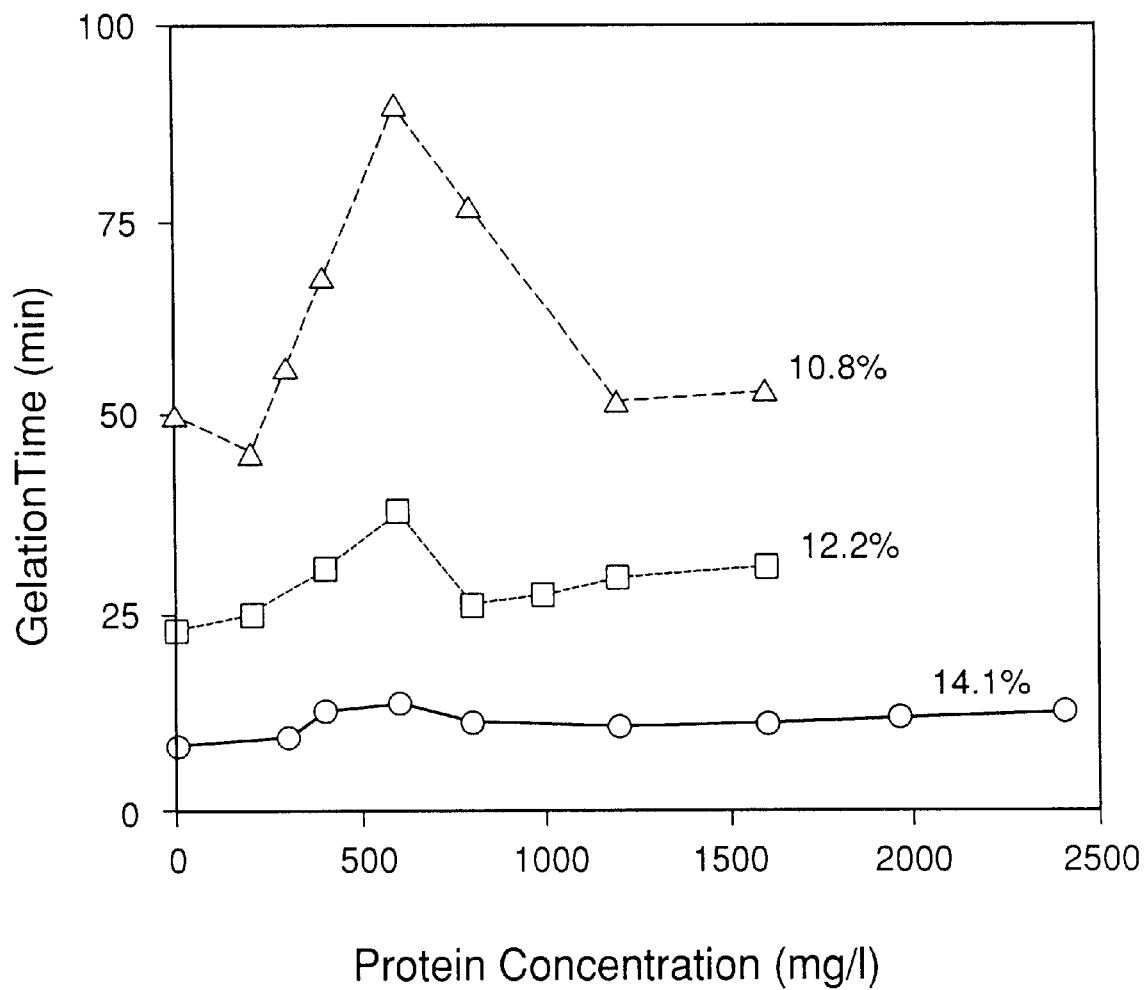
FIG. 6 graphically displays the effect of hemoglobin concentration on gelation time of silica sols of different solid concentrations at a constant pH 7.2. Each curve is labeled with the solid concentration in volume percent.

FIG. 6 shows the gelling kinetics, represented by gelation time (tg), of the colloidal solutions with different amounts of hemoglobin, at a constant pH 7.2. At an intermediate protein concentration, tg was generally found to increase as the solid fraction of silica decreased.

In comparing tg of the protein-colloid mixture (FIG. 6) with the corresponding optical absorbance (FIG. 5), an inverse relationship was observed. That is, at a higher tg of the colloidal solution, a lower optical absorbance of the encapsulated protein was observed. This indicated that hemoglobin was subject to continual conformational change once it mixed and interacted with the colloidal silica. This observation was consistent with a recent report on adsorption of hemoglobin onto ultrafine (diameter=15 nm) silica particles, which showed a large reduction in the relative absorbance to ~60% at pH 7.0 (Kondo and Fukuda, 1998). However, it also confirmed that once the gel network was formed, the trapped hemoglobin did not undergo further conformational changes. Thus, by shortening the gelation time, the conformational change could be minimized.

B. The Effect of pH on the Synthesis

Similar trends in optical characteristics and gelation kinetics were also observed when encapsulation was carried out under different pH values, but at a fixed solid fraction (14%).

Figure 7:
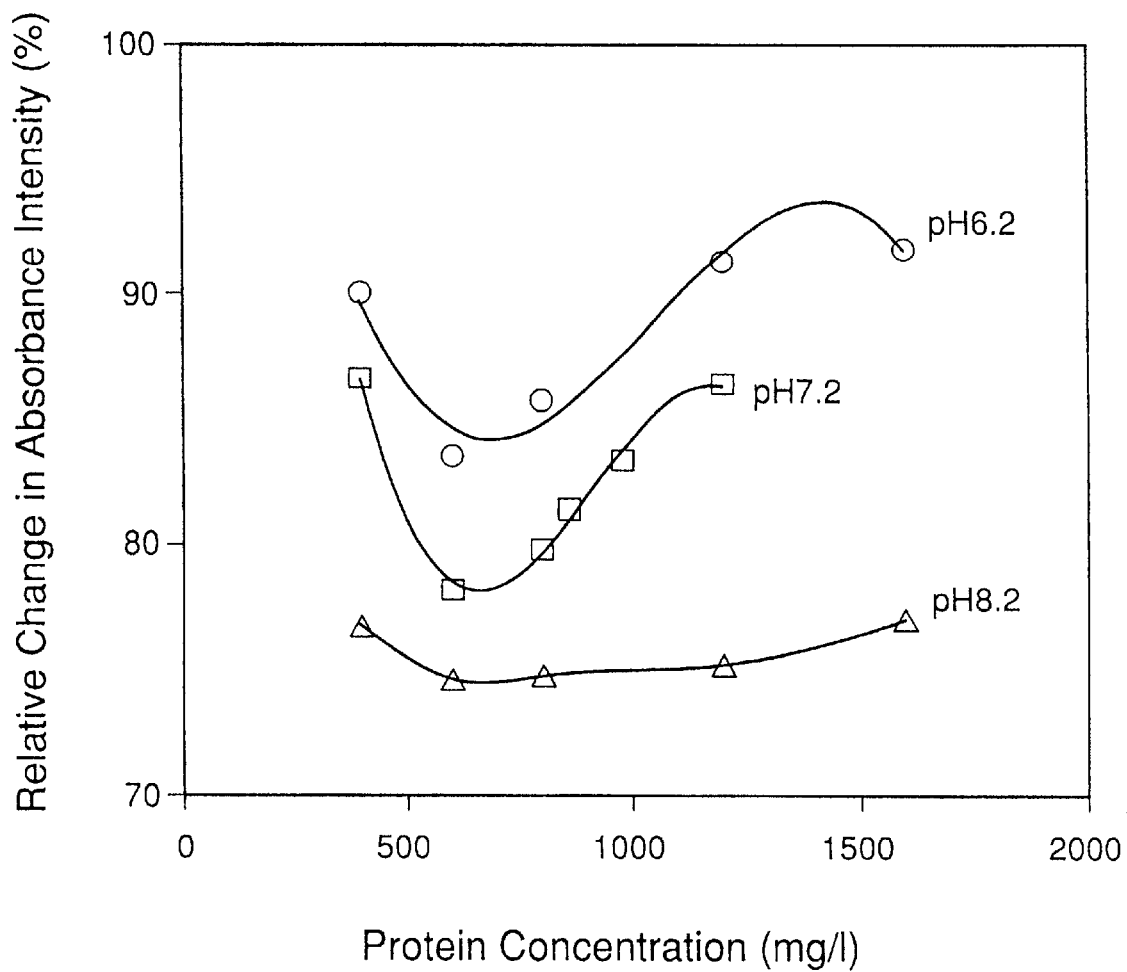
FIG. 7 graphically displays the effect of protein concentration on relative absorbance of hemoglobin encapsulated in aqueous silica gels prepared under different pH values.
Figure 8:
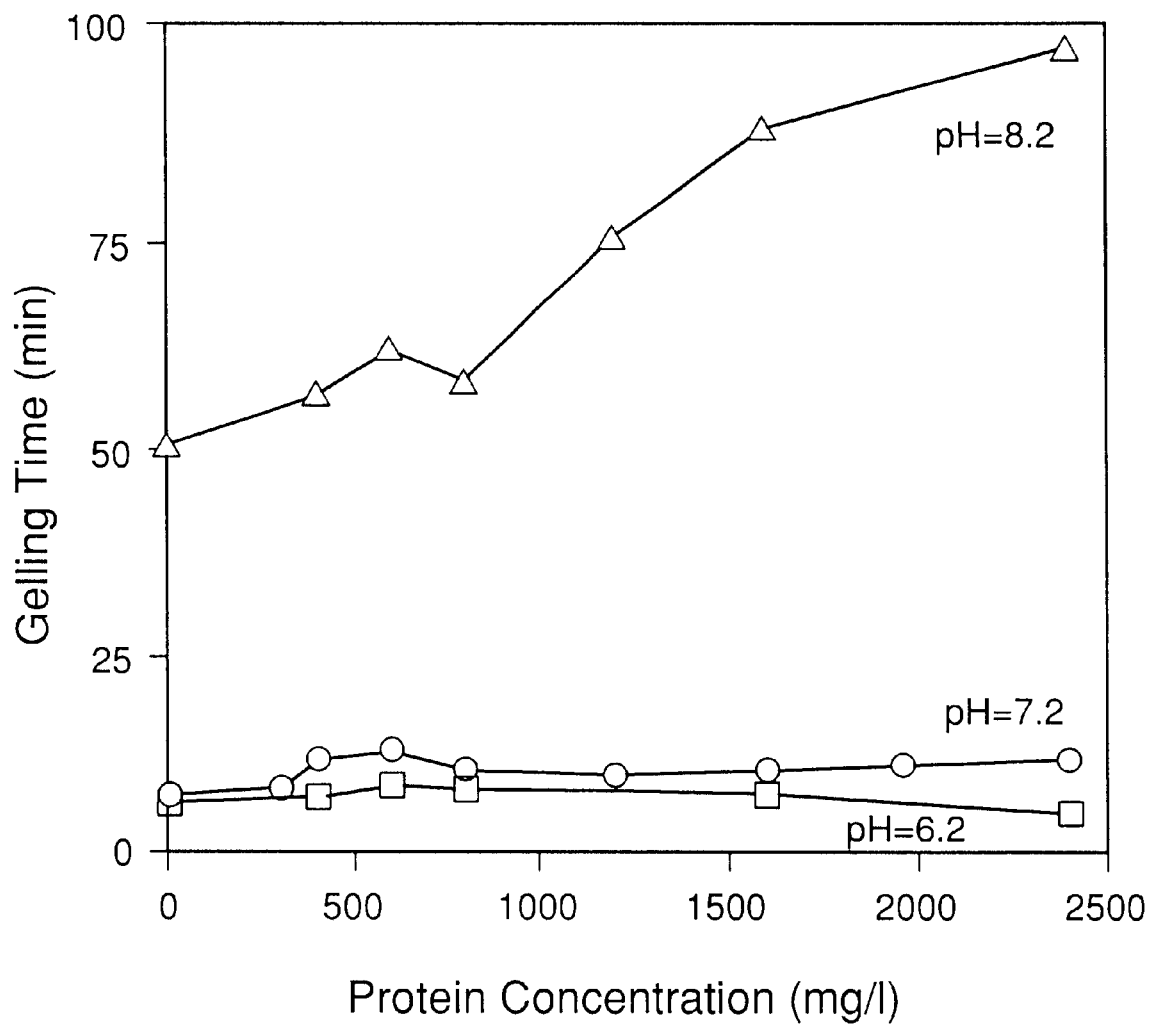
FIG. 8 graphically displays the effect of hemoglobin concentration on gelation time of silica sols prepared under different pH values.

The effect of three pH values, 6.2, 7.2 and 8.2, is shown in FIGS. 6 and 7. The U-shape curve in relative absorption became much flatter at pH 8.2, as compared with the curve observed pH 7.2 and 6.2, with a corresponding increase in absorbance. FIG. 8 shows the results of tg under different pH values. Notably, when the protein concentration exceeded ~600 mg/ml, any further increase in concentration caused different gelling behaviors; i.e., a decreased tg at pH 6.2, a slightly increased tg at pH 7.2, and a greatly increased tg at pH 8.2. Nevertheless, a consistent inverse relationship was maintained between the gelling time (FIG. 8) and the corresponding optical absorbance of the encapsulated protein (FIG. 7).

Figure 9:
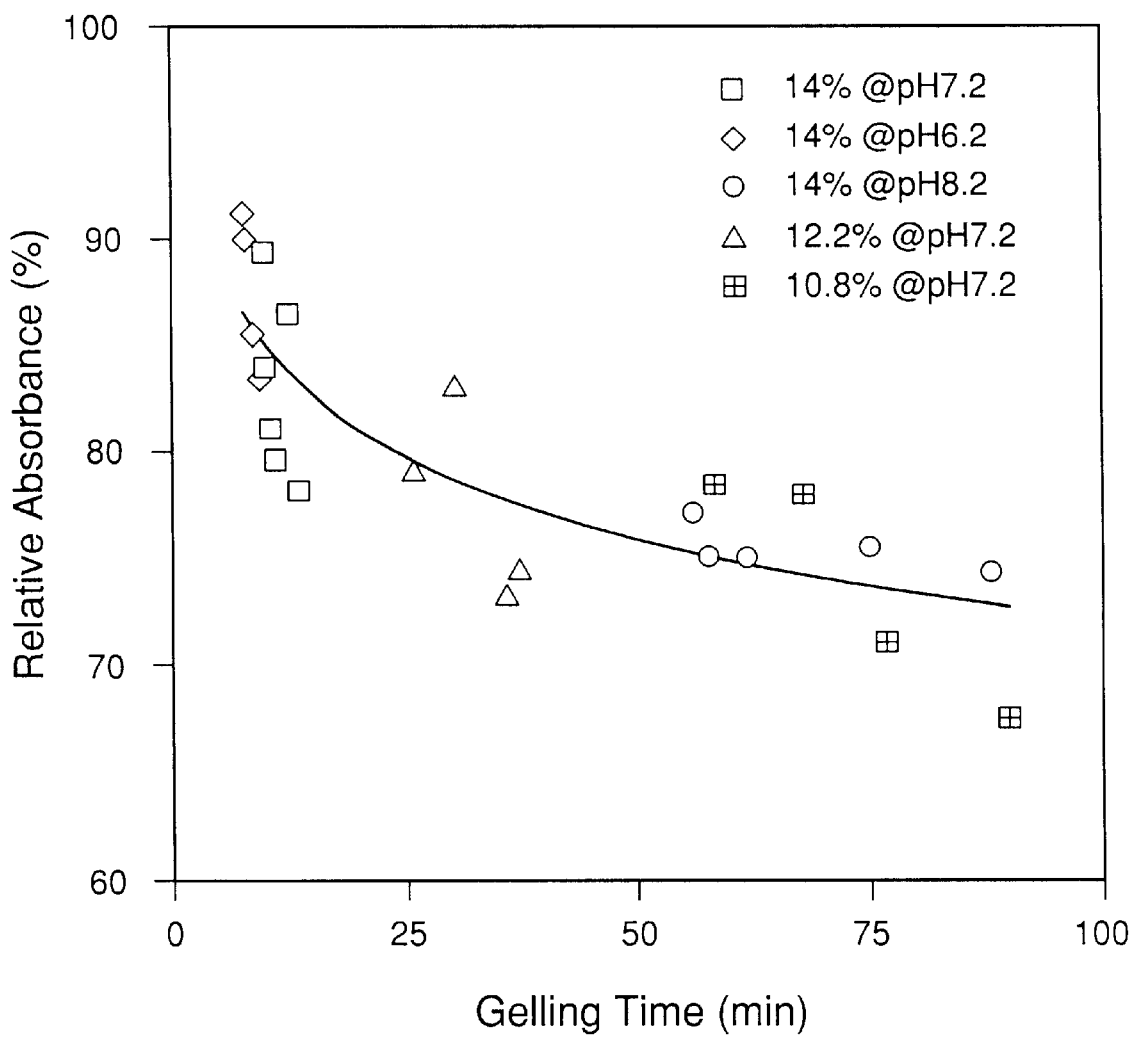
FIG. 9 graphically displays the relative absorbance of encapsulated hemoglobin in aqueous colloidal silica gels, showing the inverse relationship between absorbance and increased gelation time of the protein-sol mixtures prepared under various processing conditions.

Therefore, current results suggest that a higher rate of gelation favors stabilization of the encapsulated protein structure. In support of this proposition, FIG. 9 summarizes the correlation between tg and the corresponding optical absorbance, obtained by plotting all of the experimental data shown in FIGS. 4–7 on different solid fractions, pH, and protein concentrations. Although there are some outlying data, the trend towards a decreasing optical absorbance with increasing tg is evident. This finding strongly indicates the importance of "freezing" the host colloidal matrix in arresting the evolution of the protein structure. Improving the conformational stability of the encapsulated hemoglobin can, therefore, be achieved by optimizing the encapsulation process, i.e., by increasing the solid fraction, while decreasing the pH throughout the synthetic process.

Example 3
The Influence of Drying on Protein Conformation

In addition to the rate of gelation, the rate of driving is a significant factor in the encapsulation process. Dunn et al., 1998 suggested that proteins-containing pores behave differently from those without. Proteins without pores will shrink, and even collapse, during drying, while those with pores shrink, but conform to the dimensions of the protein. Although the Dunn study was based on an alkoxide precursor, pore shrinkage is a common phenomenon in gel drying, which is also found in the aqueous gel of the present invention. The magnitude of shrinkage, however, is much smaller in a drying aqueous colloidal, than in a drying alkoxide-based gel. This is because some solid fraction already exists in the colloidal solution.

Upon drying, the aqueous sol-gel (containing 14% solid fraction of colloidal silica) experienced shrinkage of about 62% in volume, compared to the typical shrinkage of more than 85% in volume in alkoxide-based gels. The pore size of the dried aqueous gel was also determined using the BET sorption method.

The pores had an average value of 5.3 nm in diameter, which is relatively close to the dimensions of the hemoglobin molecule. By comparison, the average pore size in dried alkoxide-based silica gels ranged from 2–3 nm (Shafer et al., *J. App. Phys.* 61[12]:5438–5446 (1987)). This is because in alkoxide gels, the later-stage contraction of the pores must be resisted by the entrapped protein.

To assess the effect of drying on conformation in the present invention, an experiment was conducted utilizing two prepared samples; one in bulk form and the other in the form of a thin film (by dip coating onto a glass substrate from a mixture identical in composition to the sample in bulk form). The hemoglobin encapsulated in each sample was monitored spectroscopically during the course of drying at 4° C. The thin film (~0.4 mm in thickness) was expected to have a much higher rate of drying than that of the bulk material under identical drying conditions.

FIG. 11 shows the resulting fractional absorbance of the two samples with respect to the drying time, together with absorbance in a buffer solution. The fractional absorbance was obtained using the optical absorbance at the time of gelation (tg.~7 min) to divide the absorbance after a specific time of drying. As shown, the hemoglobin encapsulated in the thin film demonstrated a better retention of protein conformation than when encapsulated in the bulk form. Since the total shrinkage after complete drying is the same in both the thin film and the bulk, a higher rate of pore shrinkage is apparently correlated to an improved conformational retention. Given the importance of pore size of the matrix to stabilizing the conformation of the entrapped biomolecule, it is surprising that no quantitative analysis has been previously reported on the matter.

Furthermore, as compared to the fractional absorbance of the native-state conformation when the protein is stored in buffer solution, both encapsulation forms gave a higher level of retention over time. The encapsulated proteins showed a relative absorption change of only 16% in bulk form (and ~8% in thin film) after drying for 30 days, a time sufficiently long for most practical applications.

The above results indicate that the amount of total pore shrinkage is not as important to conformation as the rate of shrinkage (assuming the proper size particle was selected to produce pore that when dried would approximate the size of the encapsulated biomaterial). Once the pore size contracts to approach the dimensions of the entrapped protein, further conformational changes are finally, fully arrested. In a thin film, pore contraction occurs rapidly, hence it produces better protein stability because there is less time for denaturation before the conformation becomes fixed.

Moreover, although buffer solution is usually a suitable environment for carrying proteins without affecting their native conformations, the mobility and flexibility of proteins in such solution is ultimately detrimental to their long term storage. An encapsulated protein was thus found to be most stable in a structurally "frozen" environment, which is provided by a pore space that is precisely the same as, or as close as possible to, the dimensions of the encapsulated molecule.

Example 4

The Stability of Gels against Harsh Environments

A. Effect of Solvents:

Methanol and ethanol were used as solvent perturbants to monitor the structural stability of the encapsulated protein by mixing the gel with the solvents for 24 h.

The solvent denaturation tests reveal that the proteins denature due to aggregation when the methanol concentration is progressively increased up to 30 vol% in buffer solution. An accompanied increase in spectral intensity (e.g., FIG. 3) is not a sign of enhanced biological activity (Bescher and Mackenzie, 1998), rather it indicates a substantial reduction in the activity (Miller et al., 1006; private communication). Thus, the present alcohol-free, aqueous sol-gel process offers an advantageous process for protein encapsulation, as an alternative to the conventional alkoxide-based approach.

Figure 12A:
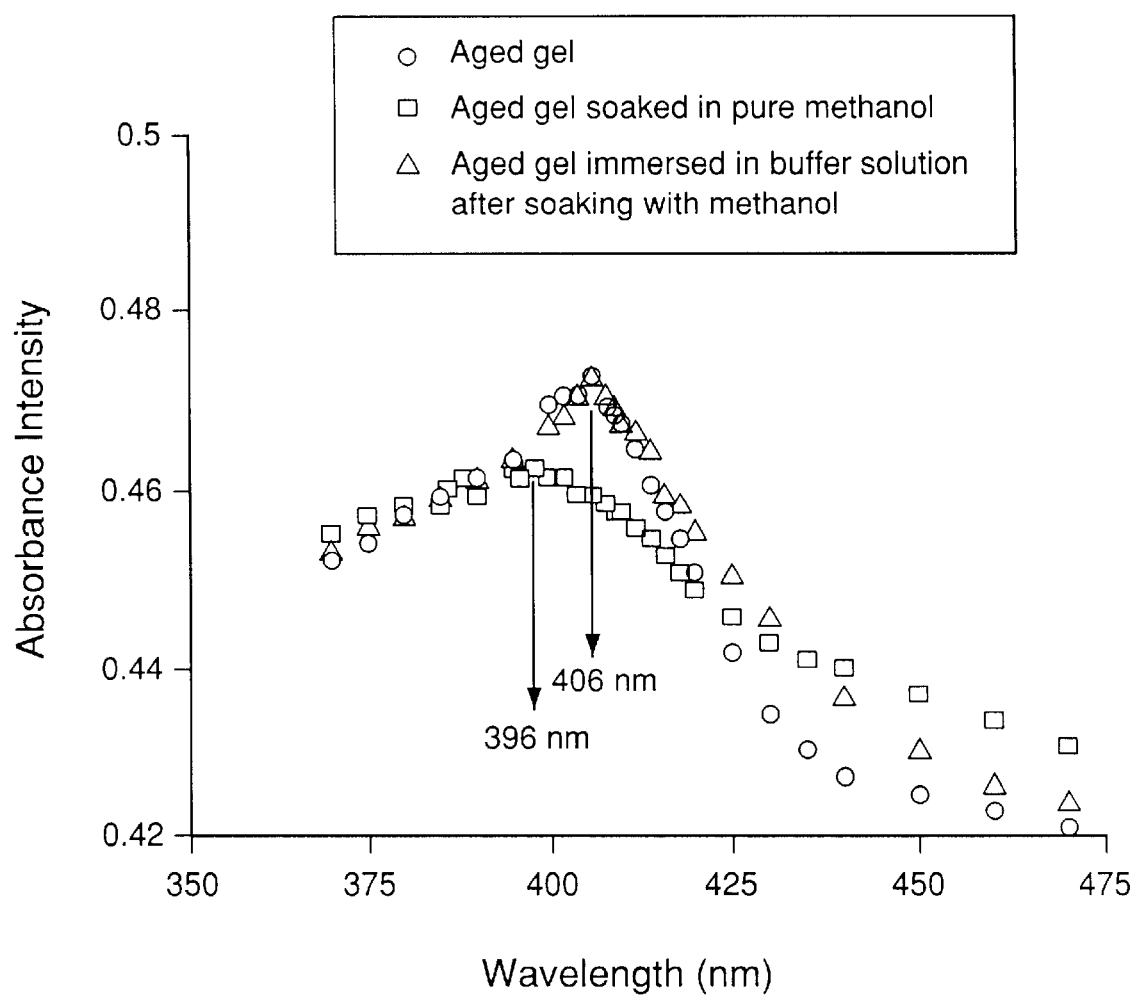
FIGS. 12A and 12B graphically depict the effect of solvent perturbation on the structural stability of the encapsulated protein.
Figure 12B:
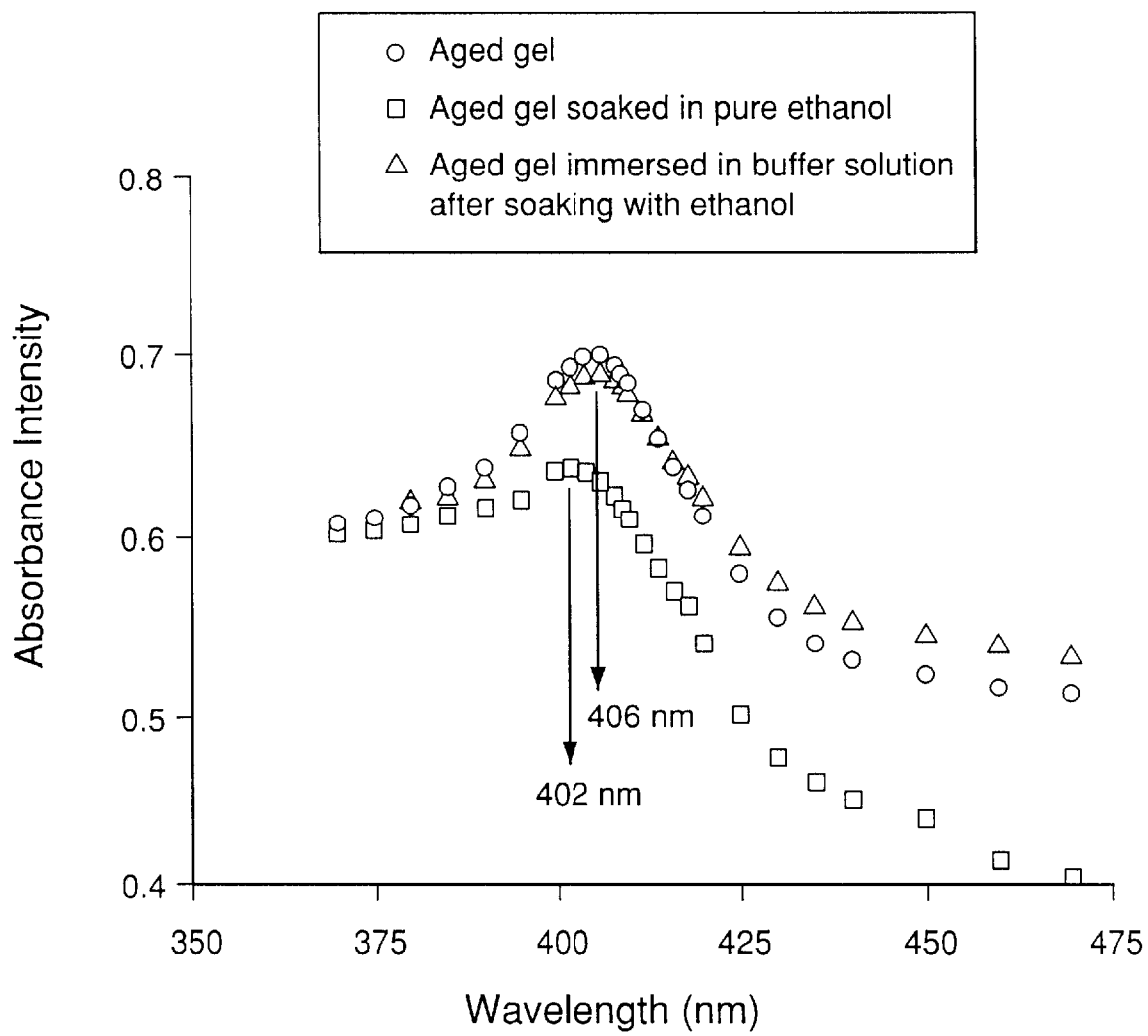

Solvent perturbation on the structural stability of the encapsulated protein is illustrated in FIGS. 12A and 12B, for methanol and ethanol, respectively. Obviously, hemoglobin molecules underwent a greater perturbation when they were in contact with methanol molecules, than when contacted with ethanol molecules. However, in both cases, the absorption spectra shifted (by 4–10 nm) and broadened (by 5–6 nm) in the solvents, but the original shape of the absorption curve is restored (to essentially the pre-perturbation condition) after immersing the protein in buffer solution.

B. Effect of Temperature

A change in thermal energy may cause a noticeable change in molecular inter-/intramolecular interactions, such as the formation and cleavage of hydrogen bonds (Nicola and Leach, *Int. J. Pept. Proteion Res*, 8:393–415 (1976)), leading to a structural change or denaturation of protein. Such changed are invariably accompanied by a change in both the spectral transition and the intensity of absorption spectrum. A recent study, by Lan et al., *J. Mater. Chem.* 9:45–53 (1999)), reported the use of absorption intensity as a measure of thermal denaturation in cytochrome c.

Figure 10:
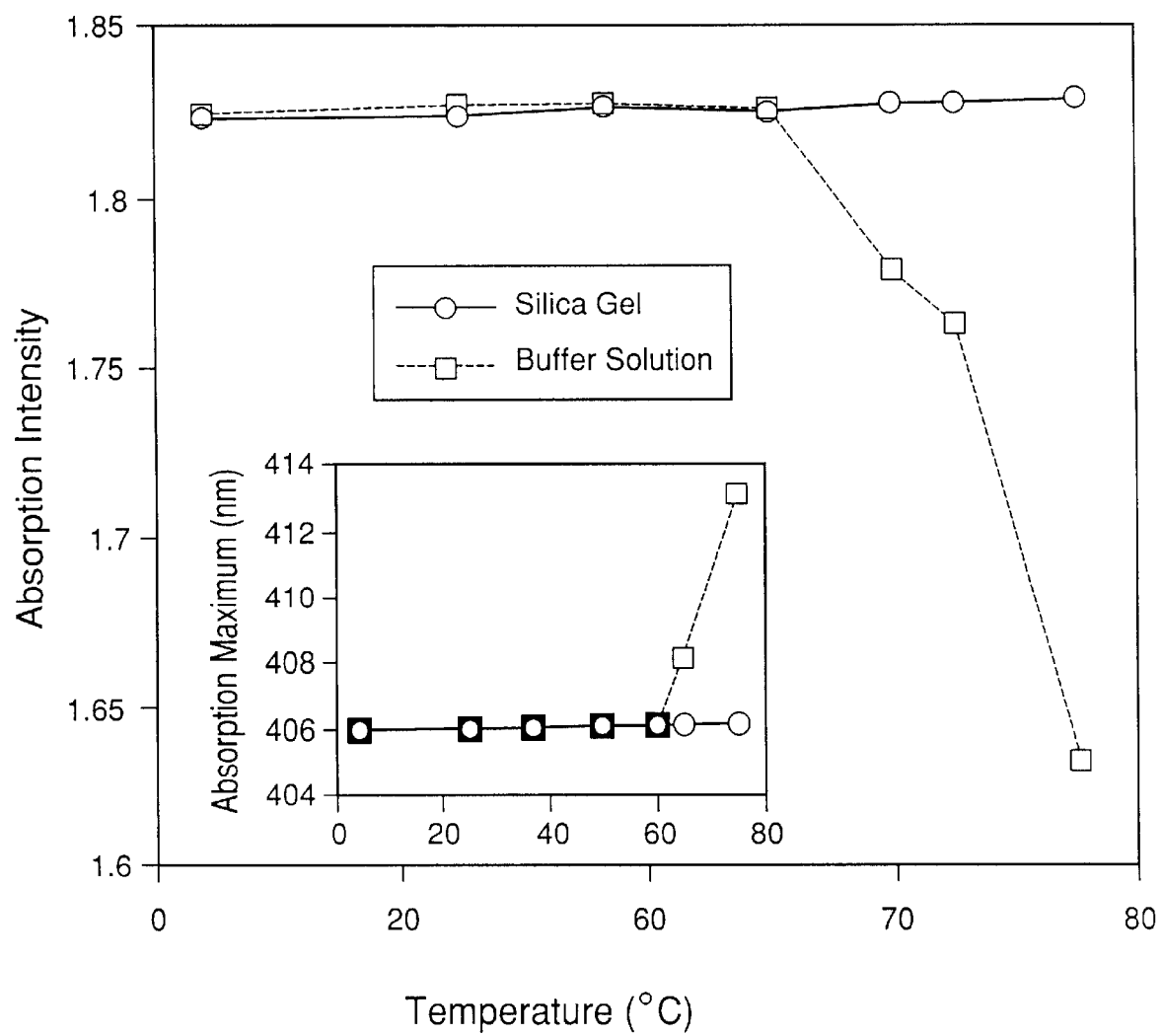
FIG. 10 graphically displays the absorption intensity of hemoglobin, plotted as a function of temperature. The inset shows that no spectral transition was detected in the gel.
Figure 11:
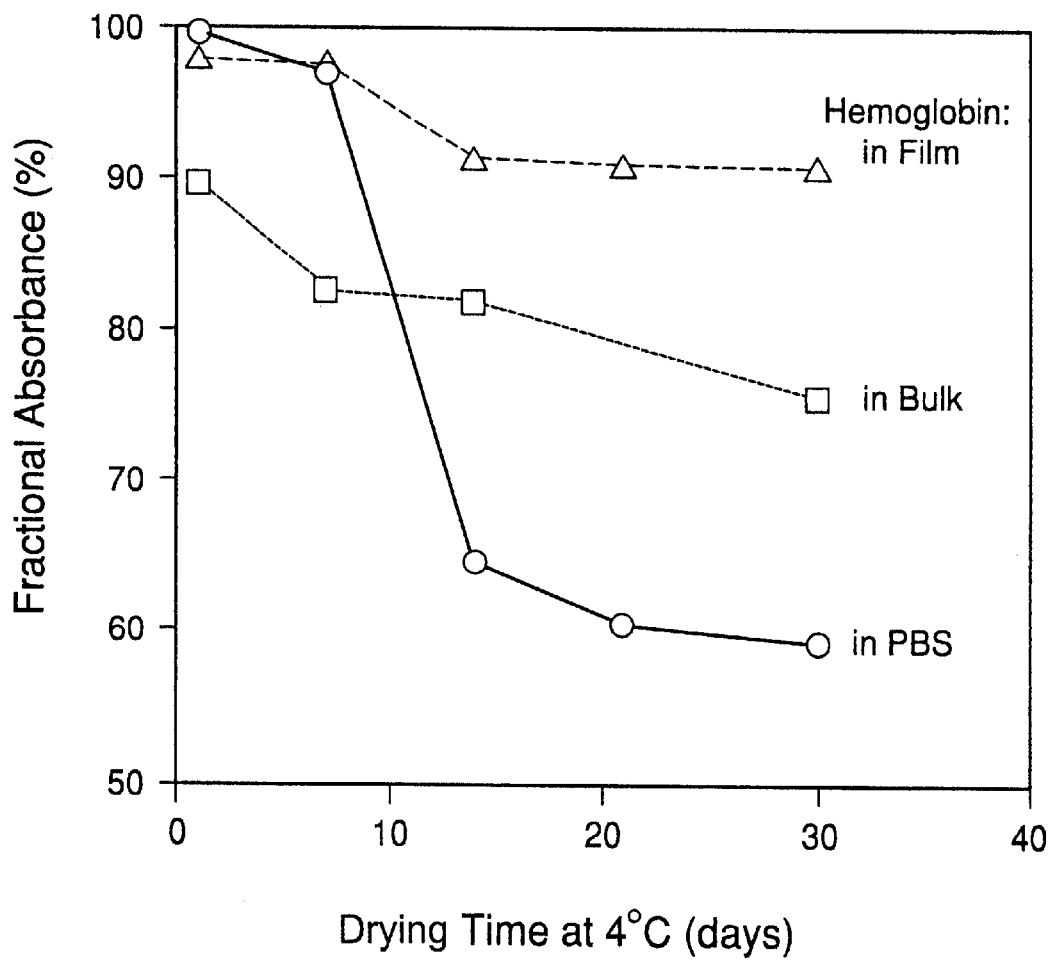
FIG. 11 graphically displays the fractional absorbance of hemoglobin encapsulated in bulk and in thin film silica matrices during 30-day drying at 4° C. Also shown is the fractional absorbance of hemoglobin in buffer solution under identical storage condition.

In this investigation, the absorption intensity of hemoglobin is plotted as a function of temperature, as shown in FIG. 10. Obviously, the absorption intensity remains unchanged for proteins trapped in the aged gel, indicating an excellent structural stability against thermal perturbation over the entire temperature range of the study.

Nevertheless, a considerable decrease in absorbance was observed in the solution at temperature greater than about 55° C. A sharp transition from 406 nm (below 55° C.) to 413 nm (at 75° C.) can also be seen in the solution; however, no spectral transition was detected in the gel (inset of FIG. 10). The protein structures remained stable within the matrix. Moreover, an increase in the stability against thermal perturbation was achieved within the pores, indicating that the physical constraints of the small pores in the present invention protect the model protein from thermal denaturation.

Example 5
Enzymatic Activity of Catalase-Doped Silica Matrices

To examine the retention of biological activity of the biomolecules after aqueous sol-gel encapsulation, bovine liver catalase was selected and characterized using aqueous hydrogen peroxide (0.4 mM $H_2O_2$) as an assay solution. The analysis of activity was conducted according to the method described by Miller et al., 1996.

Figure 13:
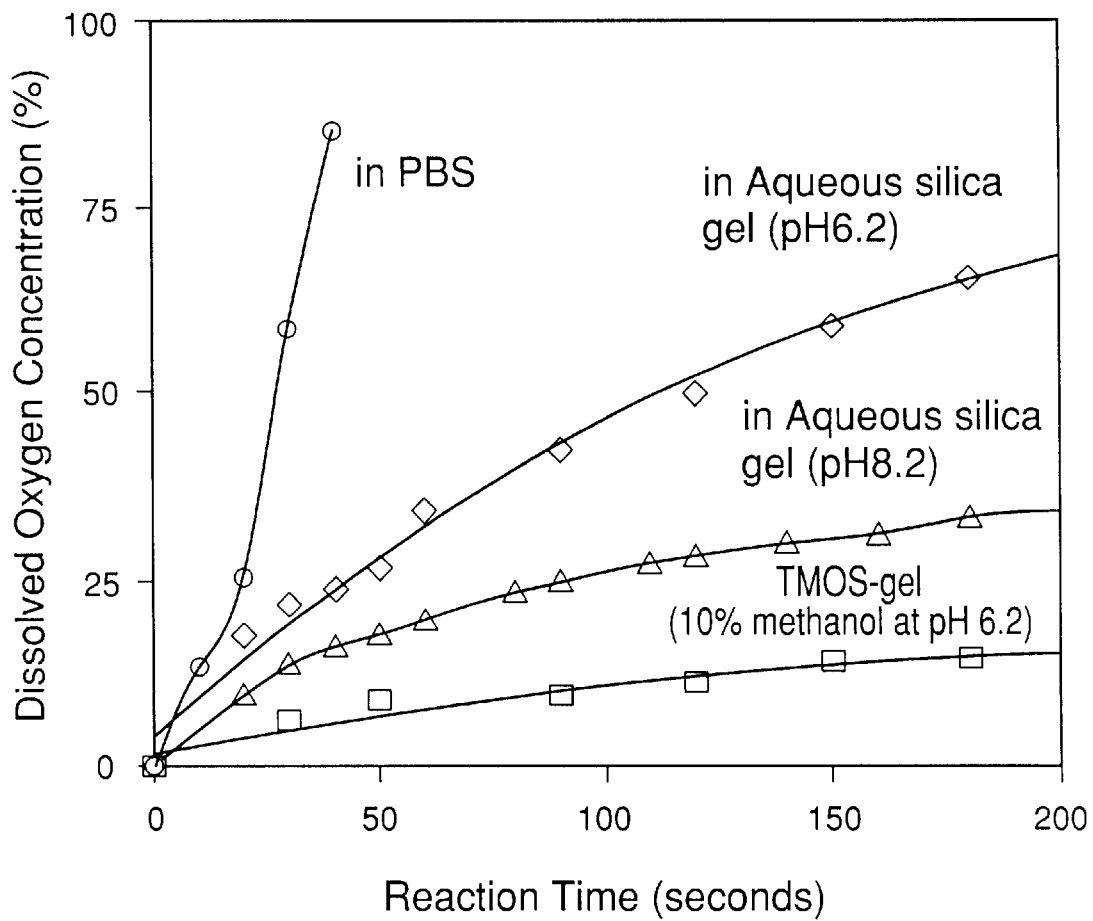
FIG. 13 graphically displays the oxygen concentration versus time generated from catalytic reactions between hydrogen peroxide assay solution and catalase, in PBS as compared with encapsulation in aqueous silica gel, pH 6.2, in aqueous gel, pH 8.2, and in TMOS gel (10% methanol), pH 6.2.

In brief, an oxygen meter (YSI Model 55 biological oxygen monitor) was submerged in the assay solution. The relative enzymatic activity of catalase was determined by monitoring the rate of oxygen evolution from the decomposition of $H_2O_2$ once the catalase-doped (with a concentration of 1.5 mg/l) dried gels (stored over 2 months at 4° C.) were immersed into the test solution. FIG. 13 shows the resulting change of oxygen concentration in the solution.

The catalytic activity in the doped gels of the present invention were further correlated to the slopes of the oxygen concentration—time profiles. The lowest slope was observed in TMOS-derived gel with 10 vol % methanol, indicating a decrease in catalytic activity of the enzyme due to denaturation, which was consistent with Miller's previously reported findings. By comparison, a significantly steeper slope was obtained when the catalase was encapsulated using the aqueous sol-gel process at pH 8.2, indicating a substantially better retention of the catalytic activity of the encapsulated enzyme. A further improvement in catalytic activity was achieved when the encapsulation was performed at lower pH values, thereby optimizing a synthesis condition of the process as described above (high solid concentration or low pH).

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. An alcohol-free method of making a porous, inorganic matrix containing a biological material encapsulated therein, comprising:

(a) forming an aqueous composition comprising a ceramic oxide colloidal sol mixed with an acidified oxide salt solution, which is transformed into a polymerizing hydroxide solution, and wherein the resulting composition has a pH ranging from 6.2 to 8.2;

(b) adding to said composition an amount of the biological material in a physiologically acceptable-buffered solution to form a nanocomposite, wherein the ionic strength of the resulting nanocomposite is adjusted to a physiologically acceptable level by the addition of salts;

(c) gently shaking the resulting nanocomposite until it becomes viscous;

(d) shaping the viscous, aqueous mixture produced in step (c) into a final form and aging into an aqueous gel; and (e) drying the aged gel slowly in air at a temperature of ~4° C., thereby permitting a portion of the water in the gel to evaporate, wherein the drying gel has a decreased volume as compared with the aged gel of step (d), and molecules of the biological material are encapsulated within pores of the drying or dried gel.

2. The method of claim 1, wherein the nanocomposite is comprised of colloidal silica sol and dissolved sodium silicate.

3. The method of claim 1, wherein the size of the sol particle is selected to produce a pore size when the gel is dried, which is essentially the same as the size of a molecule of the encapsulated biological material.

4. The method of claim 1, wherein the biological material is selected from the group consisting of RNA, DNA, active proteins, active fragments of DNA, RNA, or proteins, and cells or tissues.

5. The method of claim 4, wherein the biological material is any active protein or active fragment thereof.

6. The method of claim 5, wherein the protein or active fragment thereof is an enzyme or active compound selected from the group consisting of any RNase, DNase, nuclease, ribonuclease, hydrogenase, dehydrogenase aldase amidase, aminotransferase, amylase, anhydrase, apyrase, arginase, aspartase, aspariginase, carboxylase, carboxypeptidase, catalase, cullulase, cholinesterase, acetylcholinesterase, deaminase, dextranase, dismutase, elastase, esterase, fumarase, glucosidase, hexokinase, isomerase, invertase, kinase, lactase, lipase, lysozyme, malase, naringinase, oxidase, oxygenase, papain, pectinase, peptidase, pepsin, peroxidase, phosphodiesterase, phosphotase, protease, reductase, transferase, tyrosinase, urease, cholesterol, trypsin, chymotrypsin, enzyme, immunoglobulin, and combinations thereof.

7. The method of claim 6, wherein the protein is selected from the group consisting of cytochrome c, catalase, myoglobin, and hemoglobin.

8. The method of claim 1, wherein the aqueous gel is in the form of a monolithic gel, thin film, or fiber.

9. The method of claim 1, wherein the dried gel comprises pores having an average diameter ranging from 1 nm to 100 nm.

10. The method of claim 9, wherein the pores have an average diameter ranging from 2 nm to 50 nm.

11. The method of claim 10, wherein the dried gel comprises a matrix having pores of approximately the same dimension as the molecules of biological material encapsulated therein.

12. The alcohol-free, porous, inorganic, colloidal sol-gel nanocomposite having encapsulated therein an active biological material, wherein the nanocomposite is prepared in accordance with the method of claim 1.

13. The nanocomposite of claim 12, comprising colloidal silica sol and dissolved sodium silicate.

14. The nanocomposite of claim 13, wherein the encapsulated biological material is selected from the group consisting of RNA, DNA, proteins, active fragments of DNA, RNA, or proteins, and cells or tissues.

15. The nanocomposite of claim 14, wherein the encapsulated biological material is any active protein or active fragment thereof.

16. A method for the quantitative or qualitative detection of a test substance that reacts with or whose reaction is catalyzed by an active biological material, wherein said biological material is encapsulated within a nanocomposite, and wherein said nanocomposite comprises a porous, inorganic matrix prepared by an alcohol-free colloidal sol-gel method, said quantitative or qualitative method comprising:
  (a) preparing the nanocomposite comprising said active biological material encapsulated within a porous, inorganic matrix prepared by an alcohol-free colloidal sol-gel method;
  (b) bringing said biological-material-containing nanocomposite into contact with a gas or aqueous solution comprising the test substance; and
  (c) quantitatively or qualitatively detecting, observing or measuring the change in one or more characteristics in the biological material encapsulated within the nanocomposite.

17. The method of claim 16, wherein a change in one or more characteristics of the encapsulated biological material is qualitatively or quantitatively measured by spectroscopy, utilizing one or more techniques selected from the group consisting of UV, IR, visible light, fluorescence, luminescence, absorption, emission, excitation and reflection.

18. A method of storing a biological material in a porous, inorganic matrix, wherein withstanding exposure to adverse conditions, more than 80% of the biological activity of the material is retained for at least 2 months, comprising:
  (a) forming an aqueous composition comprising a ceramic oxide colloidal sol mixed with an acidified oxide salt solution, which is transformed into a polymerizing hydroxide solution, and wherein the resulting composition has a pH ranging from 6.2 to 8.2;
  (b) adding to said composition an amount of the biological material to be stored in a physiologically acceptable-buffered solution to form a nanocomposite, wherein the ionic strength of the resulting nanocomposite is adjusted to a physiologically acceptable level by the addition of salts;
  (c) gently shaking the resulting nanocomposite until it becomes viscous;
  (d) shaping the viscous, aqueous mixture produced in step (c) into a final form and aging into an aqueous gel;
  (e) drying the aged gel slowly in air at a temperature of ~4° C., thereby permitting a portion of the water in the gel to evaporate, wherein the drying gel has a decreased volume as compared with the aged gel of step (d), and molecules of the biological material are stably encapsulated within pores of the drying or dried gel; and
  (f) storing the gel of step (e) and the biological material encapsulated therein.

19. The method of storing a biologically active material in a porous, inorganic matrix in accordance with claim 19, wherein the biological material is an active protein or active protein fragment, wherein the nanocomposite comprises colloidal silica sol and dissolved sodium silicate, and wherein withstanding exposure to adverse conditions, more than 80% of the biological activity of the protein or protein fragment is retained for at least 2 months.

20. The method of storing a biologically active material in a porous, inorganic matrix in accordance with claim 18, wherein withstanding exposure to adverse conditions, more than 80% of the biological activity of the material is retained for at least 1 year.

21. The active biological material, which has been stored in accordance with claim 18 for at least 2 months, but wherein more than 80% of the biological activity of the material has been retained.

* * * * *